United States Patent
Ahn et al.

(10) Patent No.: US 9,353,399 B2
(45) Date of Patent: May 31, 2016

(54) TWO-PHOTON ABSORBING COMPOUND WITH METHODS OF SYNTHESIS AND USE

(71) Applicants: Kyo Han Ahn, Pohang-si (KR); Dokyoung Kim, Geoje-si (KR)

(72) Inventors: Kyo Han Ahn, Pohang-si (KR); Dokyoung Kim, Geoje-si (KR)

(73) Assignee: POSTECH ACADEMY-INDUSTRY FOUNDATION, Pohang-Si, Gyeongsangbuk-Do (KR)

(*) Notice: Subject to any disclaimer, the term of this patent is extended or adjusted under 35 U.S.C. 154(b) by 0 days.

(21) Appl. No.: 14/345,137

(22) PCT Filed: Mar. 21, 2013

(86) PCT No.: PCT/KR2013/002335
§ 371 (c)(1),
(2) Date: Mar. 14, 2014

(87) PCT Pub. No.: WO2013/172544
PCT Pub. Date: Nov. 21, 2013

(65) Prior Publication Data
US 2014/0377791 A1 Dec. 25, 2014

(30) Foreign Application Priority Data
May 17, 2012 (KR) .......................... 10-2012-0052711

(51) Int. Cl.
| | |
|---|---|
| *C12Q 1/26* | (2006.01) |
| *C07C 255/42* | (2006.01) |
| *C07D 311/92* | (2006.01) |
| *C07C 221/00* | (2006.01) |
| *C07C 223/06* | (2006.01) |
| *C07C 255/43* | (2006.01) |
| *C07D 311/58* | (2006.01) |
| *C07F 7/18* | (2006.01) |
| *C12Q 1/42* | (2006.01) |
| *C07C 253/30* | (2006.01) |

(52) U.S. Cl.
CPC ............... *C12Q 1/26* (2013.01); *C07C 221/00* (2013.01); *C07C 223/06* (2013.01); *C07C 253/30* (2013.01); *C07C 255/42* (2013.01); *C07C 255/43* (2013.01); *C07D 311/58* (2013.01); *C07D 311/92* (2013.01); *C07F 7/1852* (2013.01); *C12Q 1/42* (2013.01); *G01N 2333/90638* (2013.01); *G01N 2800/2835* (2013.01); *G01N 2800/304* (2013.01)

(58) Field of Classification Search
CPC .......... C12Q 1/26; C12Q 1/42; C07D 221/00; C07D 223/06; C07D 263/00; C07D 255/42; C07D 311/58; C07D 311/92; C07F 7/1852
See application file for complete search history.

(56) References Cited

U.S. PATENT DOCUMENTS

2009/0155837 A1 6/2009 Cho
2009/0286275 A1 11/2009 Cho

OTHER PUBLICATIONS

Kim et al. Asian J. Org. Chem. (Sep. 2012; published online Jul. 2, 2012) 1(1): 60-64.*
Kim et al. Chem. Comm (2012; published online Aug. 31, 2012) 48: 10243-10245.*
D. Kim et al; Reaction-based two-photon probes for in vitro analysis . . . ; Chem. Comm.; 2012; vol. 48; pp. 6833-6835.
W. Denk et al; Two-photon laser scanning fluorescence microscopy; Science Mag; 1990; vol. 248; pp. 73-76.
W.R. Zipfel et al; Nonlinear magic: multiphoton microscopy in the biosciences; Nat. Biotechnol.; 2003; vol. 21; No. 11; pp. 1369-1377.
F. Helmchen et al; Deep tissue two-photon microscopy; Nature Methods; vol. 2; No. 12; 2005; pp. 932-940; pp. 235.
H.M. Kim et al; Environment-sensitive two-photon probe for intracellular free . . . ; Angew. Chem. Int. Ed.; vol. 46; 2007; pp. 3460-3463.
H.M. Kim et al; A two-photon fluorescent probe for calcium waves in living tissue; Angew. Chem. Int. Ed.; vol. 46; 2007; pp. 7445-7448.
J.H. Lee et al; A two-photon fluorescent probe for thiols in live cells and tissues; J. Am. Chem. Soc.; vol. 132; 2010; pp. 1216-1217.
M.E. Jun et al; "Turn-on" fluorescent sensing with "reactive" probes; Chem. Commun.; vol. 47; 2011; pp. 7583-7601.
M. Takeuchi et al; Molecular design of artificial molecular and ion recognition . . . ; Accts of Chem. Research; vol. 34; No. 11; 2001; pp. 865-873.
M.W. Peczuh et al; Peptide and protein recognition by designed molecules; Chem. Rev.; vol. 100; 2000; pp. 2479-2494.
G. Chen et al; Design of optical switches as metabolic indicators: new . . . ; J. Am. Chem. Soc.; vol. 127; 2005; pp. 4544-4545.
W. Zhou et al; New bioluminogenic substrates for monoamine oxidase assays; J. Am. Chem. Soc.; vol. 128; 2006; pp. 3122-3123.
A.E. Albers et al; Activity-based fluorescent reporters for monoamine oxidases . . . ; Chem. Commun.; 2007; pp. 4647-4649.
J. Aw et al; Synthesis and characterization of . . . ; Chem. Asian J.; vol. 5; 2010; pp. 1317-1321.
M. Santra et al; A chemodosimeter approach to fluorescent sensing and imaging of . . . ; Chem. Commun.; 2009; pp. 2115-2117.
M. Santra et al; fluorescent detection of palladium species with an . . . ; Chem. Commun.; vol. 46; 2010; pp. 3964-3966.
M.C.Y. Chang et al; A selective, cell-permeable optical probe for hydrogen peroxide . . . ; J. Am. Chem. Soc.; vol. 126; 2004; pp. 15392-15393.

(Continued)

*Primary Examiner* — Susan Hanley
(74) *Attorney, Agent, or Firm* — Lucas & Mercanti, LLP

(57) ABSTRACT

Disclosed is a compound which is a two-photon absorbing fluorescent substance, a production method for the compound, a fluorescence sensor and molecular probe able to sense various substrates or enzyme activity or the like using the same, and a method of sensing enzyme activity or the like using the same. The disclosed compound can be used as a fluorescence sensor, and can be used in the study and treatment of diseases in which MAO enzymes are involved such as mood disorders using MAO enzyme activity and inhibitor screening.

20 Claims, 14 Drawing Sheets

(56) References Cited

OTHER PUBLICATIONS

T. Kim et al; A fluorescent self-amplifying wavelength-responsive sensory polymer . . . ; Angew. Chem. Int. Ed.; vol. 42; 2003; pp. 4803-4806.

A.L. Garner et al; Specific fluorogenic probes for ozone in biological and atmospheric samples; Nat. Chem.; 2009; pp. 316-321.

T. Kim et al; A fluorescent turn-on probe for the detection of alkaline phosphatase . . . ; Chem. Commun.; vol. 47; 2011; pp. 9825-9827.

M.B.H. Youdim et al: Isolated Chromaffin Cells from Adrenal Medulla Contain Primarily . . . ; Science; 1984; pp. 619-621.

International Search Report dated Jun. 28, 2013.

\* cited by examiner 1 (IminoPOS)

Fig. 2

| | $\lambda_{abs}$(nm) | $\varepsilon$ (Lmol$^{-1}$cm$^{-1}$) | $\lambda_{fl}$(nm) | $\phi_F$ | $\sigma$ (GM) |
|---|---|---|---|---|---|
| IminoPOS | 446 | 12,436 | 585 | 0.67 | 126 |
| Acedan | 365 | 14,690 | 501 | 0.43 | 171 |
| Coumarin 153 | 425 | 19,280 | 548 | 0.39 | 173 |

$\lambda_{abs}$: Maximum absorption wavelength, $\varepsilon$: Mole absorbance coefficient,
$\lambda_{fl}$: Maximum emission wavelength, $\phi_F$: Fluorescence efficiency,
σ(GM): Two-photon absorption cross-section value Fig. 12
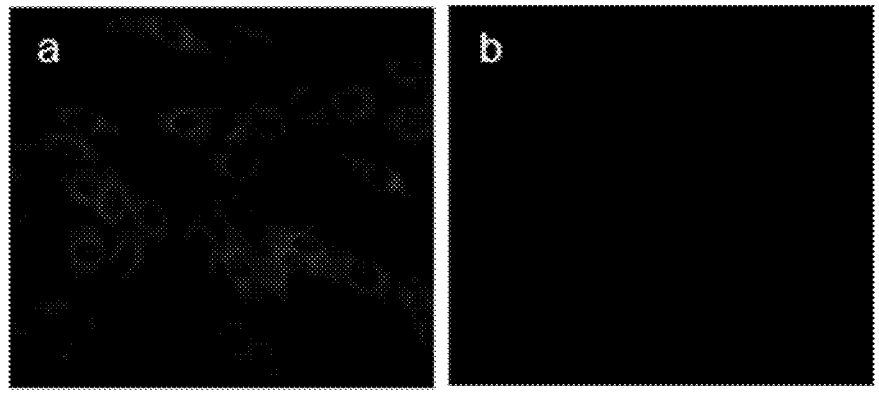
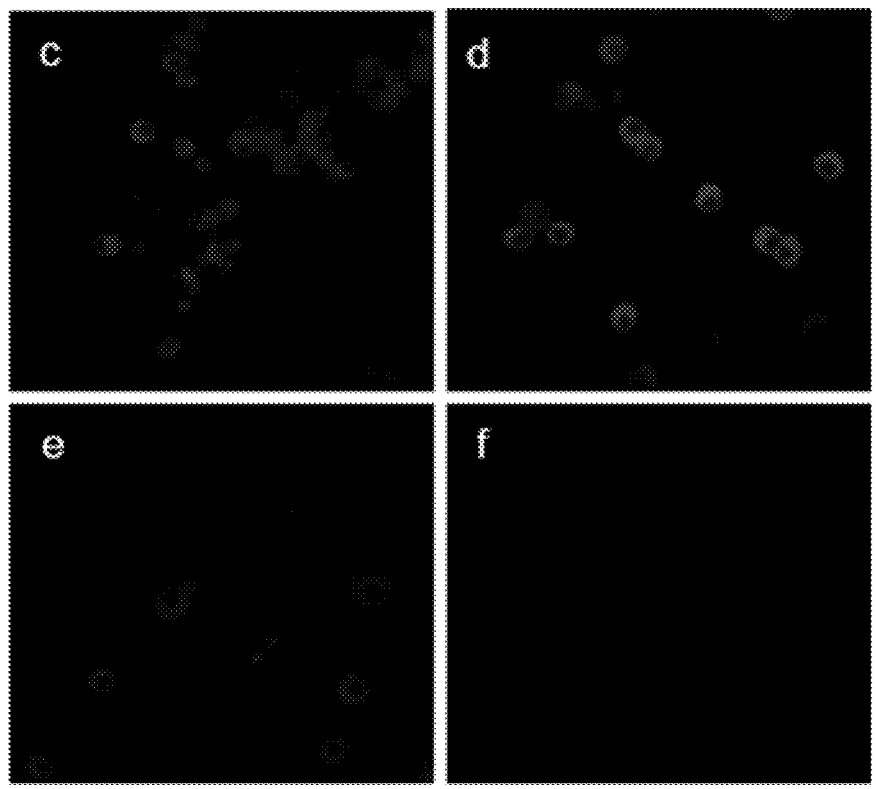

Fig. 13
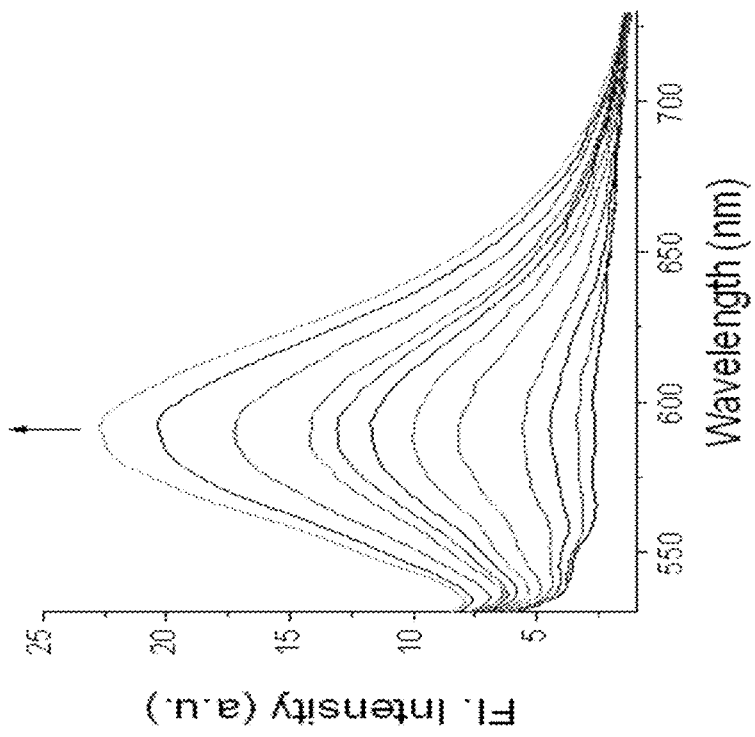
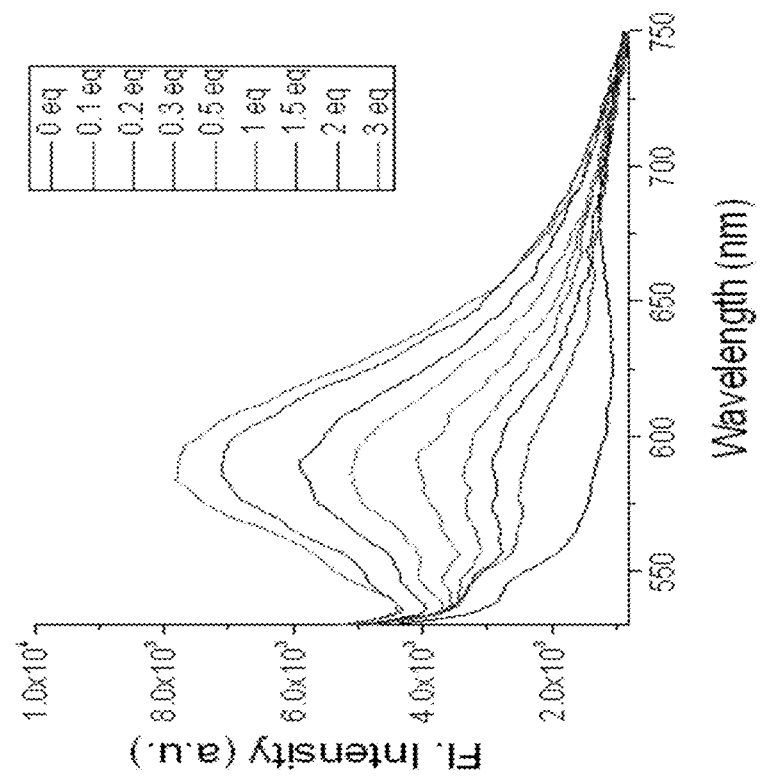

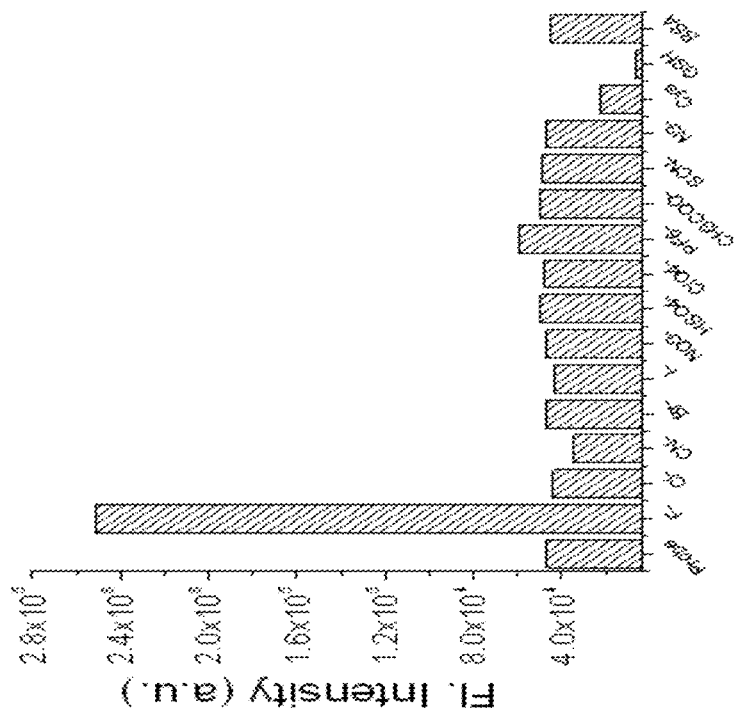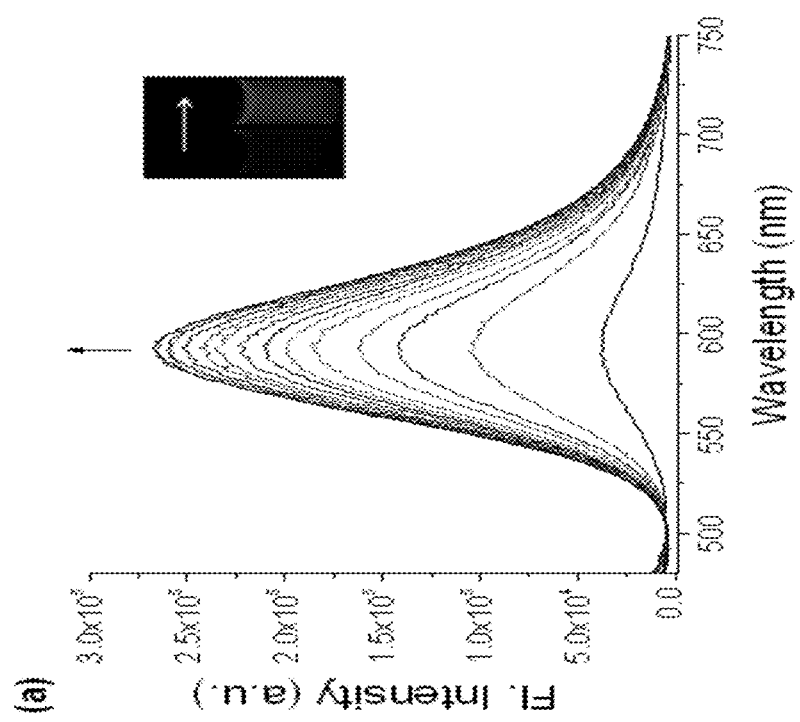
Fig. 14

TWO-PHOTON ABSORBING COMPOUND WITH METHODS OF SYNTHESIS AND USE

CROSS-REFERENCE TO RELATED APPLICATIONS

This application is a 371 of PCT/KR2013/002335, filed Mar. 21, 2013, which claims the benefit of Korean Patent Application No. 10-2012-0052711, filed May 17, 2012, the contents of each of which are incorporated herein by reference.

TECHNICAL FIELD

The present invention relates to: a compound which is a novel two-photon absorbing fluorescent substance; a production method for the compound; a fluorescence sensor and molecular probe able to sense various substrates or enzyme activity or the like by using the same; and a method of sensing enzyme activity or the like using the same. More specifically, the present invention relates to a novel two-photon absorbing fluorescent substance which has the high photo-stability of acedan which is a two-photon absorbing fluorescent substance and a large two-photon absorption cross-section value, and has the high fluorescence efficiency of coumarin which is a one-photon absorbing fluorescent substance, while exhibiting absorption and emission characteristics at a longer wavelength than existing acedan and coumarin and so being advantageous in in-vivo imaging.

BACKGROUND ART

A two-photon (TP) absorbing fluorescent substance is excited by receiving energy with a wavelength corresponding to a half of a one-photon (OP) absorbing fluorescent substance to have an excitation characteristic. As a result, the two-photon (TP) absorbing fluorescent substance has advantages of high cell permeability, low cell destruction, and a low quenching effect by a material such as hemoglobin in vivo, and has a characteristic capable of implementing a very high resolution because only a focus portion thereof is excited: (a) Denk, W. et al., Science, 1990, 248, 73; (b) Zipfel, W. R. et al., Nat. Biotechnol, 2003, 21, 1369; (c) Helmchen. F. et al., Nat. Methods, 2005, 2, 932.

Acedan (2-acyl-6-dimethylamino-naphthalene), as a representative two-photon absorbing fluorescent substance, has high photo-stability and a large two-photon absorption cross-section value, and has an advantage of providing a bright image in two-photon microscopy: (a) Kim, H. M. et al., Angew. Chem. Int. Ed, 2007, 46, 3460; (b) Kim, H. M. et al., Angew. Che,. Int. Ed. 2007, 46, 7445; (c) Lee, J. H. et al., J. Am. Chem. Soc. 2010, 132, 1216.

Coumarin is a one-photon absorbing fluorescent substance which is widely used due to high fluorescence efficiency (quantum yield), photo-stability, brightness, and the like. However, a development research of the two-photon absorbing fluorescent substance using coumarin derivatives is scarce up to now.

A method of analyzing or sensing a specific substrate includes electrical, electrochemical, thermal, magnetic, fluorimetric sensing methods, and the like. Among the methods, the fluorimetric sensing method has advantages of high sensitivity and resolution, low price, portability, and the like. Recently, as a research trend of a fluorimetric sensing probe, a reaction-based fluorescent probe accompanying a chemical reaction by responding to a substrate has received attention. The reason is that the reaction-based fluorescent probe is sensitized with the substrate to be selectively analyzed under an ambient environment in which the reaction is irreversible and complicated or an in-vivo condition (Jun, M. E. et al., Chem. Commun. 2011, 47, 7583). Up to now, researches based on the two-photon absorbing fluorescent substance of the reaction-based fluorescent probe are not particularly reported.

A representative method among methods of sensing a substrate such as an enzyme having biological characteristics is a fluorescence sensing method. Accordingly, various kinds of enzyme sensing fluorescent probes have been developed: (a) Takeuchi, M. et al., Acc. Chem. Res. 2001, 34, 865; (b) Peczuh, M. W. et al., Chem. Rev. 2000, 100, 2479. However, the enzyme sensing fluorescent probes are almost based on the one-photon absorbing fluorescent substance: (a) Chen, G. et al., J. Am. Chem. Soc. 2005, 127, 4544; (b) Zhou, W. et al., J. Am. Chem. Soc. 2006, 128, 3122; (c) Alber, A. E. et al., Chem. Commun. 2007, 4647; (d) Aw. J. et al., Chem. Asian. J. 2010, 5, 1317.

A monoamine oxidase (MAO) enzyme is an important factor of maintaining homeostasis of adrenaline, serotonin, dopamine, or the like which is a neurotransmitter. In case of nervous system diseases such as Parkinson's disease and depression, the MAO activity is not controlled and thus the diseases are generated, and in the remedy of the diseases, sensing enzyme activity has an important research value (Chen, G. et al., J. Am. Chem. Soc. 2005, 127, 4544). The MAO enzyme is divided into an MAO A and an MAO B according to a structure and characteristics.

DISCLOSURE

Technical Problem

In order to solve the conventrional technology problems, an object of the present invention is to provide a compound of Chemical Formula 1 which is a novel two-photon absorbing fluorescent substance, compounds of Chemical Formula 2, Chemical Formula 3, Chemical Formula 4, and Chemical Formula 5, which are precursors thereof, and a manufacturing method thereof.

Further, an object of the present invention is to provide a detection probe capable of sensing monoamine oxidase (MAO) using a compound of the following Chemical Formula 3 or Chemical Formula 4.

Further, an object of the present invention is to provide a measuring method of MAO enzyme activity and a screening method of an MAO enzyme inhibitor using a compound of the following Chemical Formula 3 or Chemical Formula 4.

Further, an object of the present invention is to provide a cell imaging method using the compounds of Chemical Formula 1 to Chemical Formula 5.

Further, an object of the present invention is to provide a detection probe capable of sensing specific substrates by introducing the following R groups in a compound of Chemical Formula 5. Here, six R groups and specific substrates corresponding thereto are as follows.

The R groups and the specific substrates include vinyl ether-mercury ion (Hg ion), propargyl ether-palladium ion (Pd ion), 4-boronato-benzyl ether-hydrogen peroxide ($H_2O_2$), t-butyldimethylsilyl ether-fluoride ion (F ion), homoallyl ether-ozone ($O_3$), and phosphate-phosphatase.

Further, an object of the present invention is to provide a production method of a compound which introduces vinyl ether as an R group in the compound of the following Chemical Formula 5 and a production method of a compound which introduces t-butyldimethylsilyl ether as an R group in the compound of the following Chemical Formula 5.

However, the object of the present invention is not limited to the aforementioned description, and other objects which are not mentioned above will be apparent to those skilled in the art from the disclosure to be described below.

Technical Solution

In order to achieve the above object, an exemplary embodiment of the present invention provides a compound of Chemical Formula 1 and a manufacturing method thereof As an exemplary embodiment of the present invention, the compound of Chemical Formula 1 may be a one-photon or two-photon absorbing fluorescent substance.

Further, when a compound of Chemical Formula 2 which is a precursor of the compound of Chemical Formula 1 reacts with a substrate, since a reactive site is broken and an intramolecular cyclization reaction occurs to generate the compound of Chemical Formula 1 having a fluorescence characteristic, the compound of Chemical Formula 2 may be used as a detection probe.

As a result, an exemplary embodiment of the present invention provides the compound of Chemical Formula 2 and a production method thereof, and a detection probe including the same.

Further, an exemplary embodiment of the present invention provides a compound of Chemical Formula 5 and a production method thereof. An exemplary embodiment of the present invention provides a production method of a compound introducing dimethyl ether and t-butyldimethylsilyl ether. The introduced R groups selectively respond to specific substrates to be hydrolyzed. The R groups introducible in the compound of Chemical Formula 4 and the respective substrates of the introduced compound are as follows; vinyl ether-mercury ion (Hg ion), propargyl ether-palladium ion (Pd ion), 4-boronato-benzyl ether-hydrogen peroxide ($H_2O_2$), t-butyldimethylsilyl ether-fluoride ion (F ion), homoallyl ether-ozone ($O_3$), and phosphate-phosphatase. Further, an exemplary embodiment of the present invention provides a detection probe for each specific substrate including the compound introducing each R group. That is, in an exemplary embodiment of the present invention, R in Chemical Formula 5 provides a detection probe of a mercury ion (Hg ion) including a compound in which R is vinyl ether in Chemical Formula 5, a detection probe of a palladium ion (Pd ion) including a compound in which R is propargyl ether in Chemical Formula 5, a detection probe of hydrogen peroxide ($H_2O_2$) including a compound in which R is 4-boronato-benzyl ether in Chemical Formula 5, a detection probe of a fluoride ion (F ion) including a compound in which R is t-butyldimethylsilyl ether in Chemical Formula 5, a detection probe of ozone ($O_3$) including a compound in which R is homoallyl ether in Chemical Formula 5, and detection probe of a phosphatase including a compound in which R is a phosphate in Chemical Formula 5.

Meanwhile, the compounds of Chemical Formula 3 and Chemical Formula 4, as compounds which introduce propylamine reactive sites into the compound of Chemical Formula 5, can be used as a detection probe for monoamine oxidase (MAO) because the MAO enzyme breaks the propylamine reactive sites to generate the compound of Chemical Formula 1.

As a result, an exemplary embodiment of the present invention provides compounds of Chemical Formula 3 and Chemical Formula 4, a production method thereof, and a detection probe for sensing MAO activity including the same.

The present inventors confirmed the activity of MAO and an effect of the enzyme inhibitor using a fluorescence sensor including the compound of Chemical Formula 3. Further, the present inventors confirmed whether a cell expresses the MAO using the fluorescence sensor.

Therefore, the present invention provides an MAO enzyme activity (enzyme kinetics) measurement and a screening method of the MAO enzyme inhibitor using the compound.

The present inventors confirmed that a fluorescence characteristic of the compound of Chemical Formula 1 can be used in cell imaging. Therefore, the present invention provides a cell imaging method using the compounds of Chemical Formula 1 to Chemical Formula 5.

Advantageous Effect

The two-photon absorbing fluorescent substance (Chemical Formula 1, called IminoPOS) introduced in the present invention has a high two-photon absorption cross-section, quantum yield, and photo-stability. Further, the two-photon absorbing fluorescent substance is used in an in-vivo imaging study according to absorption and emission in a longer wavelength compared with acedan and coumarin as existing fluorescent substances. The two-photon absorbing fluorescent substance has significantly high fluorescence sensitivity even in a one-photon microscope as well as a two-photon microscope. Accordingly, the two-photon absorbing fluorescent substance can be used as a detection probe having high sensitivity and selectivity for each substrate using precursors (Chemical Formulas 2 to 5) of the compound of Chemical Formula 1. Particularly, the two-photon absorbing fluorescent substance can be used in the study and treatment of diseases in which MAO enzymes are involved such as Parkinson's disease and depression using the compound of Chemical Formula 3 or Chemical Formula 4 in MAO enzyme activity and inhibitor screening.

DESCRIPTION OF DRAWINGS

FIG. 2 is a diagram comparing optical characteristics of acedan, coumarin 153, and compound 1 (IminoPOS).

FIG. 12(a) is a two-photon electron microscope result of a C6 glioma cell treated with the compound of Chemical Formula 1. FIG. 12(b) is a two-photon electron microscope result of a C6 glioma cell treated with a compound of Chemical Formula 3. FIG. 12(c) is a two-photon electron microscope result of a Chromaffin cell treated with the compound of Chemical Formula 1. FIG. 12(d) is a two-photon electron microscope result of a Chromaffin cell treated with the compound of Chemical Formula 3. FIG. 12(e) is a two-photon electron microscope result of a Chromaffin cell treated with the compound of Chemical Formula 3 and moclobemide. FIG. 12(f) is a two-photon electron microscope result of a Chromaffin cell treated with the compound of Chemical Formula 3 and pargyline.

FIG. 13 is a result (left graph) illustrating that fluorescence is increased according to a concentration increase of mercuric ions ($HgCl_2$) as a result of measurement, and further, is a result (right graph) illustrating that fluorescence is increased as time passes as a result of measuring a fluorescence change with time after adding mercuric ions of 3 µM.

FIG. 14 is measures that the fluorescence is increased with time after adding fluoride ions (NaF) of 20 mM as a result of measurement (left graph), and further, is a result of measuring that only fluoride ions are selectively reacted to induce a fluorescence increase as a result of verifying the fluorescence increase after adding various kinds of negative ions in addition to a compound 15 at a concentration of 20 µM (right graph). The fluorescence intensity of the right graph is measured at 595 nm.

BEST MODE

The present inventors developed a novel two-photon absorbing fluorescent substance, and invented an MAO enzyme activity sensing two-photon fluorescent probe using a precursor thereof. The present research completed the present invention by verifying optical characteristics of the fluorescent substance and establishing MAO enzyme activity in a cell.

A compound 1 (IminoPOS), as a newly developed two-photon absorbing fluorescent substance, has a skeletal system combining structures of acedan and coumarin. As a result, the compound 1 has high fluorescence efficiency and a large two-photon absorption cross-section value. Further, as compared with existing acedan or coumarin, the compound 1 shows long wavelength absorption and emission characteristics to have an advantage to imaging in vivo (see FIG. 1).

Figure 5:
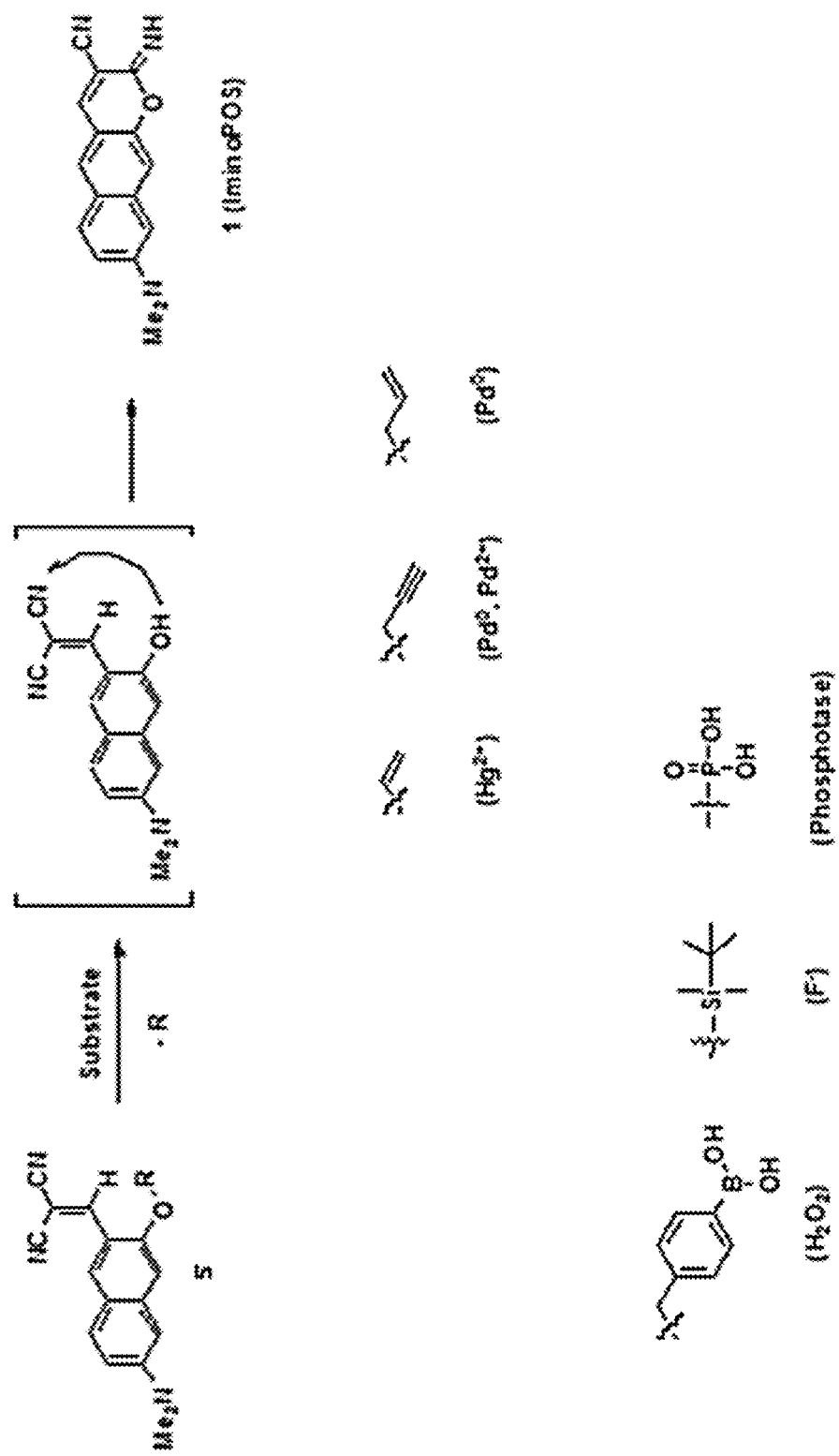
FIG. 5 illustrates a structure of a compound of Chemical Formula 5 and a compound generation reaction mechanism of Chemical Formula 1.

A compound of Chemical Formula 2 and a compound of Chemical Formula 5 are precursor structures of the compound 1. After reacting with a substrate by introducing a reactive site of which a bond is broken by a specific substrate, an irreversible intramolecular cyclization reaction is caused to generate the IminoPOS which is the two-photon absorbing fluorescent substance. Accordingly, the compounds in themselves may be used as a fluorescent molecular probe for a specific substrate, and further, may be developed as another fluorescent probe by introducing a reactive site suitable for a substrate to be analyzed as an R group of the compound of Chemical Formula 5 (see FIG. 5). As a result, the introducible reactive site to be introduced and the analyzable substrate are as follows.

Articles in brackets disclose contents that each reaction group may selectively react with each substrate, and all compounds introducing each reaction group are novel.

TABLE 1

| R group which can be introduced in Chemical Formula 5 | Analyzable substrate | Related articles |
| --- | --- | --- |
| Vinyl ether | Mercury ion (Hg ion) | (Santra, M. et al. Chem. Commun. 2009, 2115) |

TABLE 1-continued

| R group which can be introduced in Chemical Formula 5 | Analyzable substrate | Related articles |
|---|---|---|
| Propargyl ether | Palladium ion (Pd ion) | (Santra, M. et al. Chem. Commun. 2010, 46, 3964) |

Figure 11:
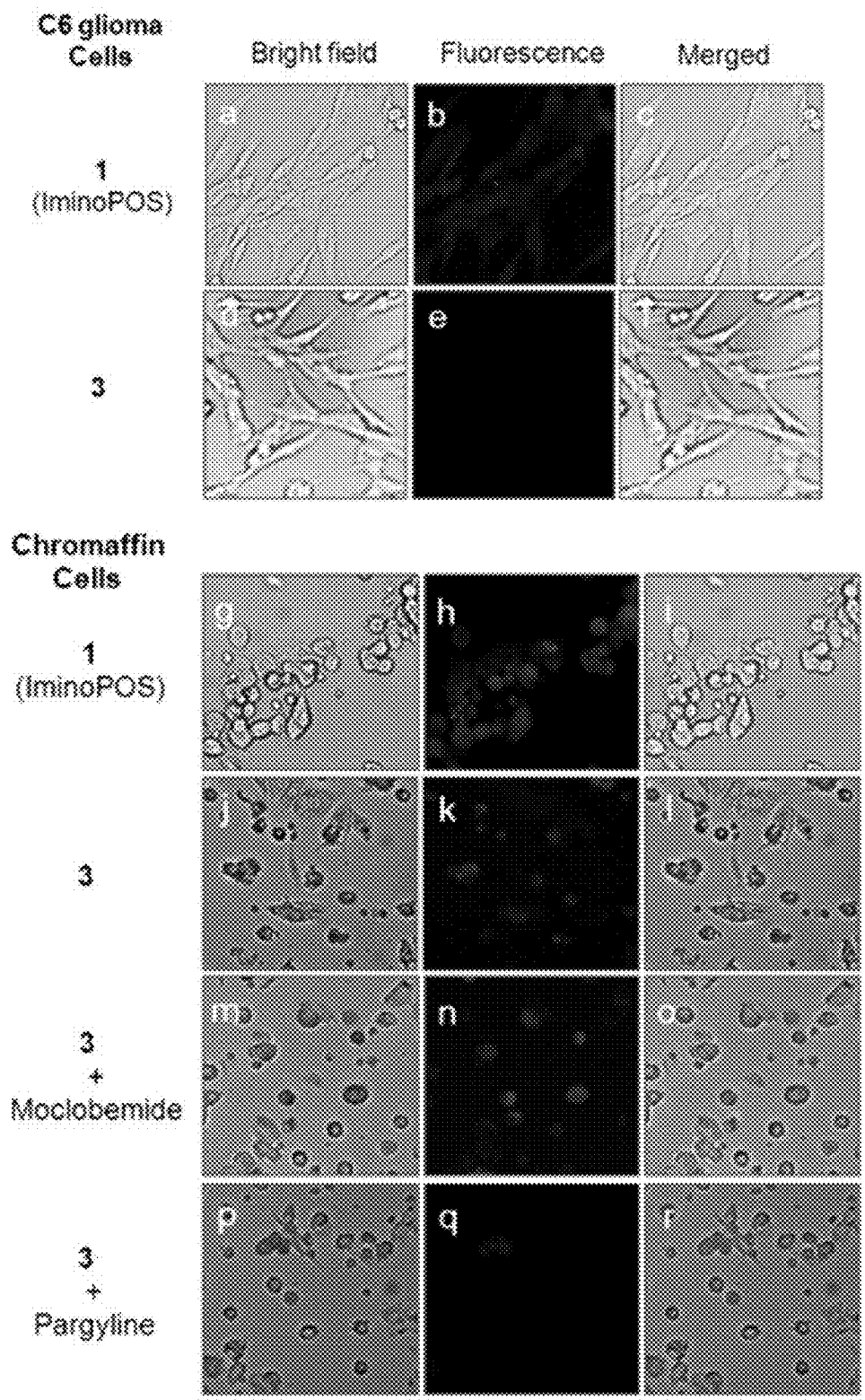
FIG. 11(a) is a bright field result of a C6 glioma cell treated with the compound of Chemical Formula 1.
FIG. 11(b) is a one-photon electron microscope result of a C6 glioma cell treated with a compound of Chemical Formula 1.
FIG. 11(c) is a merged result of a C6 glioma cell treated with a compound of Chemical Formula 1.
FIG. 11(d) is a bright field result of a C6 glioma cell treated with the compound of Chemical Formula 3.
FIG. 11(e) is a one-photon electron microscope result of a C6 glioma cell treated with the compound of Chemical Formula 3.
FIG. 11(f) is a merged result of a C6 glioma cell treated with a compound of Chemical Formula 3.
FIG. 11(g) is a bright field result of a Chromaffin cell treated with the compound of Chemical Formula 1.
FIG. 11(h) is a one-photon electron microscope result of a Chromaffin cell treated with the compound of Chemical Formula 1.
FIG. 11(i) is a merged result of a Chromaffin cell treated with a compound of Chemical Formula 1.
FIG. 11(j) is a bright field result of a Chromaffin cell treated with the compound of Chemical Formula 3.
FIG. 11(k) is a one-photon electron microscope result of a Chromaffin cell treated with the compound of Chemical Formula 3.
FIG. 11(l) is a merged result of a Chromaffin cell treated with a compound of Chemical Formula 3.
FIG. 11(m) is a bright field result of a Chromaffin cell treated with the compound of Chemical Formula 3 and moclobemide.
FIG. 11(n) is a one-photon electron microscope result of a Chromaffin cell treated with the compound of Chemical Formula 3 and moclobemide.
FIG. 11(o) is a merged result of a Chromaffin cell treated with a compound of Chemical Formula 3 and moclobemide.
FIG. 11(p) is a bright field result of a Chromaffin cell treated with the compound of Chemical Formula 3 and pargyline.
FIG. 11(q) is a one-photon electron microscope result of a Chromaffin cell treated with the compound of Chemical Formula 3 and pargyline.
FIG. 11(r) is a merged result of a Chromaffin cell treated with a compound of Chemical Formula 3 and pargyline.

Finally, using the compound 3, the MAO activities in a C6 glioma cell and a Chromaffin cell were observed (see FIGS. 11 and 12).

As described above, it is apparent that the compounds of the present invention may be used as a fluorescence sensor having high sensitivity and selectivity.

Accordingly, it will be expected that it may be useful for screening the MAO enzyme activity and the like and the enzyme inhibitor using the compounds.

A general synthesis path of the compound 1 is represented by the following Scheme 1.

[Scheme 1]

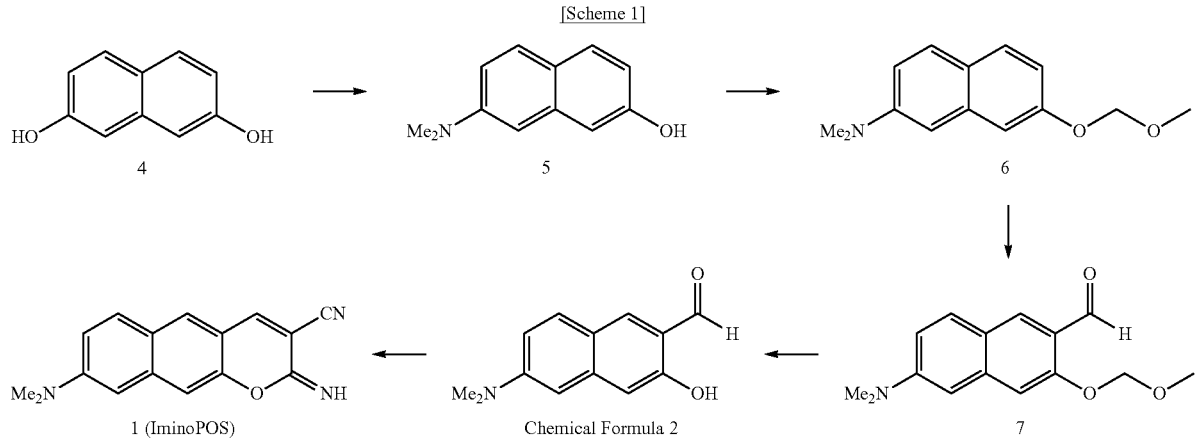

TABLE 1-continued

| R group which can be introduced in Chemical Formula 5 | Analyzable substrate | Related articles |
|---|---|---|
| 4-boronato-benzyl ether | Aqueous hydrogen peroxide ($H_2O_2$) | (Chang, M. et al. J. Am. Chem. Soc. 2004, 126, 15392) |
| t-butyldimethylsilyl ether | Fluoride ion (F ion) | (Kim, T. et al. Angew. Chem. Int. Ed. 2003, 42, 4803) |
| Homoallyl ether | Ozone ($O_3$) | (Garner, AL et al. Nat. Chem. 2009, 1, 316) |
| Phosphate | Phosphatase | (Kim, T. et al. Chem. Commun. 2011, 47, 9825) |

A synthesis method of a mercury probe and a fluoride probe and NMR data are disclosed in Example 10 and Example 11.

Chemical Formulas 3 and 4 are two-photon probes in which propylamine reactive sites are introduced in order to sense an MAO enzyme. The MAO enzyme reacts with the propylamine reactive site to break the site ((a) Chen, G. et al., J. Am. Chem. Soc. 2005, 127, 4544; (b) Zhou, W. et al., J. Am. Chem. Soc. 2006, 128, 3122; (c) Alber, A. E. et al., Chem. Commun. 2007, 4647), and then generates IminoPOS through an intramolecular cyclization reaction. The activity of the MAO enzyme is verified by measuring fluorescence intensity of the IminoPOS through a two-photon optical microscope (see FIG. 2).

Figure 3:
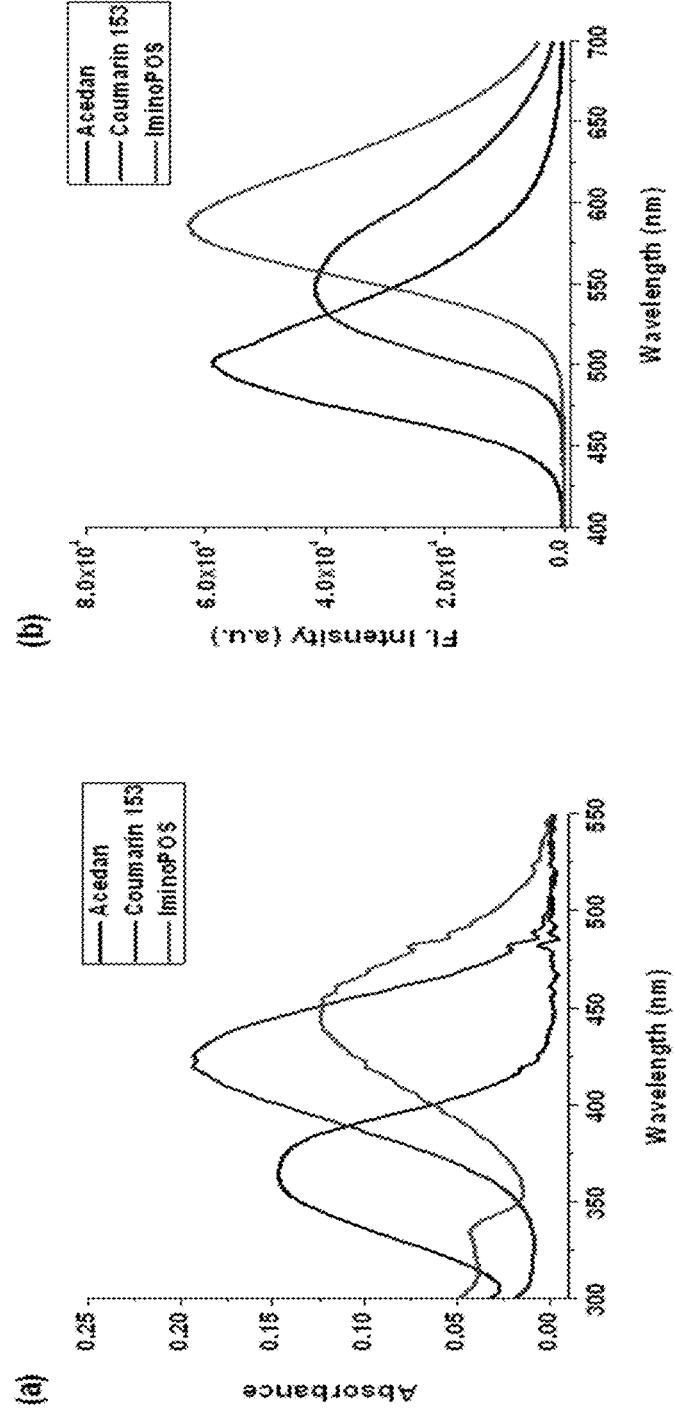
FIG. 3(a) illustrates absorption graphs of acedan, coumarin 153, and compound 1.
FIG. 3(b) illustrates emission graphs of acedan, coumarin 153, and compound 1.
Figure 4:
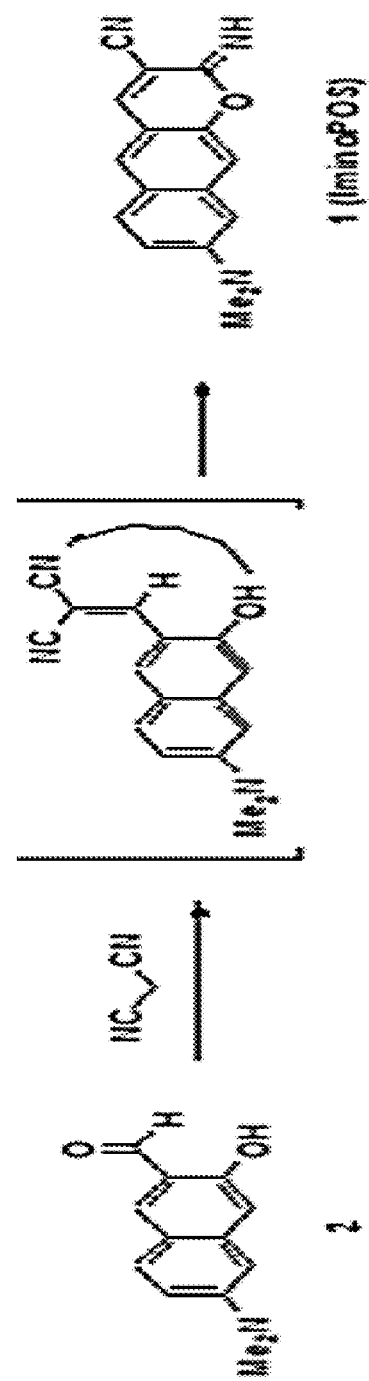
FIG. 4 illustrates a structure of a precursor (Chemical Formula 2) of compound 1 and a compound generation reaction mechanism of Chemical Formula 1.
Figure 6:
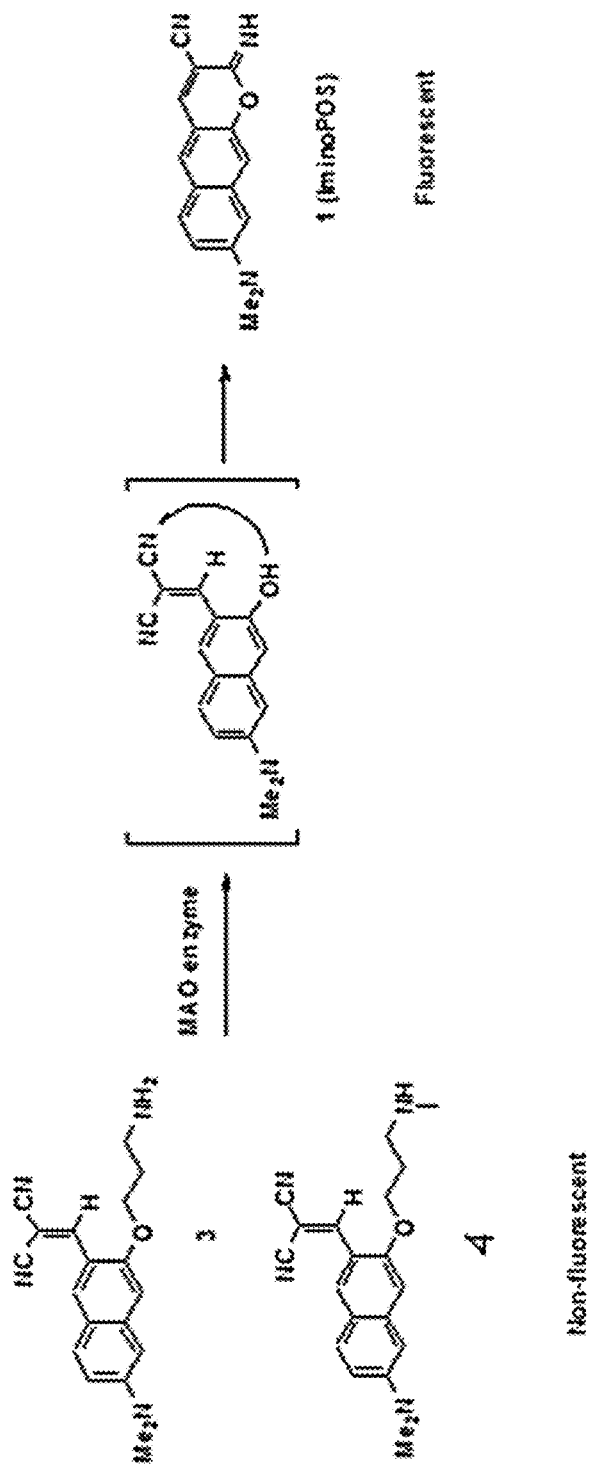
FIG. 6 illustrates a reaction mechanism for an MAO enzyme of an MAO activity sensing two-photon fluorescent probe (compounds of Chemical Formula 3 and 4).
Figure 7:
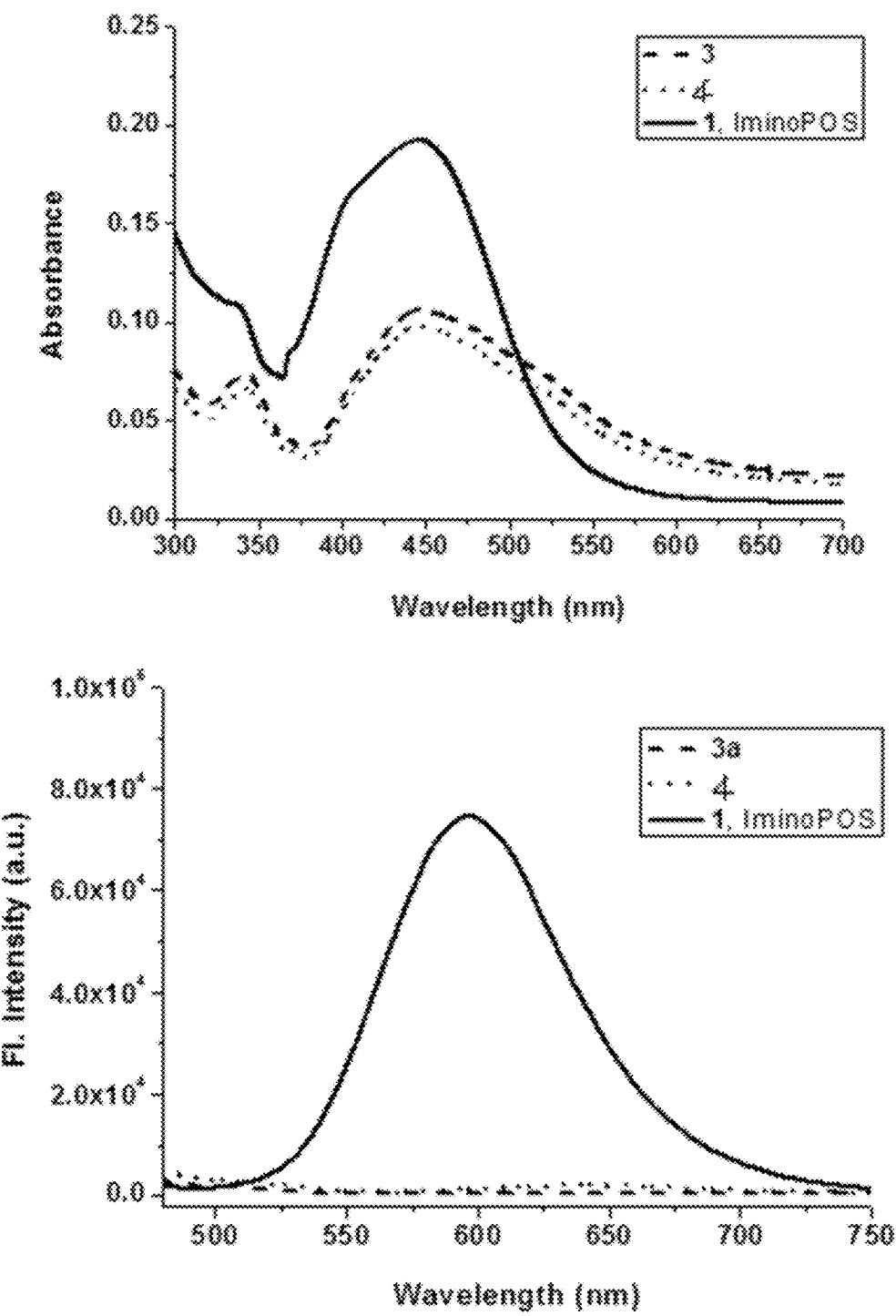
FIG. 7 illustrates absorption (upper) and emission (lower) spectrums in a buffer solution of compounds of Chemical Formulas 1, 3, and 4.

The fluorescence characteristics of the compounds 1, 3, and 4 were measured in a buffer solution, and fluorescence turn-on characteristics are shown (see FIGS. 3, 4, and 6). In addition, an activity experiment of the enzyme inhibitor was performed through an experiment of adding moclobemide and pargyline which are inhibitors of the MAO enzyme.

Hereinafter, preferable Examples for understanding the present invention will be described. However, the following Examples are just provided in order to more easily understand the present invention, and the contents of the present invention are not limited to the following Examples.

EXAMPLE 1

Synthesis of Compounds of Chemical Formula 2 and Chemical Formula 1

(1) Synthesis of 7-(dimethylamino)naphthalen-2-ol (compound 5 of Scheme 1)

The present inventors performed a synthesis of 7-(dimethylamino)naphthalen-2-ol.

8 mL of water ($H_2O$) and 10.5 mL of a dimethylamine solution (40% in $H_2O$, 93.5 mmol) were added in a sealed-tube containing 3 g of a compound 4 (18.7 mmol, Sigma-aldrich, D116408) which was a synthesis starting material and 7.11 g of sodium metabisulphite ($Na_2S_2O_5$, 37.4 mmol), and the sealed-tube was blocked. The mixture was stirred for 8 hours at 150° C. using a silicon oil container. Next, after a temperature of the reactant was cooled to room temperature (25° C.), the container was opened, 100 mL of dichloromethane, 100 mL of water, and 30 mL of saturated salt water were added, and then an organic layer was extracted by using a separating funnel. The organic layer was dried by 5 g of anhydrous sodium sulfate ($Na_2SO_4$), and concentrated by using an aspirator (at 25° C. and 20 to 500 mmHg). A light-brown solid compound obtained thus was separated (eluent: 20% EtOAc/Hexane) by using a column chromatography method (6 cm of diameter, 15 cm of height) using a silica gel (Merck-silicagel 60, 230-400 mesh) to obtain 2.10 g of a white solid compound 5 (60%). A product was analyzed by using a thin layer chromatography (TLC) (silical gel 60F-254 glass plate, Merck) to have an elution value of $R_f$=0.25 (20%

EtOAc/Hexane—eluting once). $^1$H NMR (CDCl$_3$, 300 MHz, 293K): δ 7.66-7.59(m, 2H), 7.05-7.02(m, 1H), 6.96-6.95(d, 1H), 6.85-6.82(m, 1H), 6.78-6.77(d, 1H), 5.10(s, 1H), 3.05(s, 6H). $^{13}$C NMR (CDCl$_3$, 75 MHz, 293K): δ153.88, 149.17, 136.24, 129.39, 128.61, 122.44, 114.22, 113.80, 108.02, 105.32, 40.91. HRMS: m/z calcd. for C$_{12}$H$_{13}$NO 187.0997 found 187.0999.

(2) Synthesis of 7-(methoxymethoxy)-N,N-dimethylnaphthalen-2-amine (compound 6 of Scheme 1)

The present inventors performed a synthesis of 7-(methoxymethoxy)-N,N-dimethylnaphthalen-2-amine.

In detail, 235 mg of sodium hydride (NaH, 5.875 mmol) was added in 5 mL of an N,N-dimethylformamide (DMF) solvent, an argon balloon was put, and then a temperature was decreased to −15° C. using saturated salt water and ice. 1 g of a compound 5 (5.34 mmol) was dissolved in 5 mL of DMF, and then slowly dropped into the mixed solution for about 5 minutes while the temperature was maintained. During the process, H$_2$ gas was generated, passed through a silicon oil trap, and then discharged outside. It was verified that the mixed solution was stirred for 1 hour at the same temperature and then bubbles (H$_2$ gas) were not generated any more in the trap. Subsequently, 0.4 mL of chloromethyl methyl ether (5.34 mmol) was slowly dropped for about 5 minutes. When the dropping was completed, the temperature was changed to the room temperature of 25° C., and the chloromethyl methyl ether was stirred for 6 hours. After 6 hours, 100 mL of water was added, and extraction was performed using 200 mL of ethyl acetate (EtOAc). In the extracted organic layer (EtOAc), water existing in the organic layer was dried with 10 g of anhydrous sodium sulfate. The dried ethyl acetate organic layer was concentrated by using an aspirator. A light-brown liquid compound obtained thus was separated (eluent: 5% EtOAc/Hexane) through a column chromatography method (6 cm of diameter, 15 cm of height) using a silica gel to obtain 988 mg of a white solid compound 6 (80%). The product was analyzed by using a thin layer chromatography to have an elution value of R$_f$=0.45 (20% EtOAc/Hexane—eluting once). $^1$H NMR (CDCl$_3$, 300 MHz, 293K): δ7.75(d, 1H), 7.72(d, 1H), 7.40-7.39(d, 1H), 7.15-7.08(m, 2H), 6.98-6.97 (d, 1H), 5.39(s, 2H), 3.69(s, 3H), 3.11(s, 6H). $^{13}$C NMR (CDCl$_3$, 75 MHz, 293K): δ 155.75, 149.16, 136.23, 129.11, 128.55, 123.00, 114.99, 114.58, 108.69, 105.96, 94.62, 56.07, 40.83. HRMS: m/z calcd. for C$_{14}$H$_{17}$NO$_2$ 231.1259 found 231.1262.

(3) Synthesis of 6-(dimethylamino)-3-(methoxymethoxy)-2-naphthaldehyde

The present inventors performed a synthesis of 6-(dimethylamino)-3-(methoxymethoxy)-2-naphthaldehyde (compound 7 in Scheme 1).

In detail, 2.2606 g of a compound 6 (9.774 mmol) was added in a 100 mL round-bottom flask, and an argon balloon was put. Thereafter, 50 mL of ethyl ether (Et$_2$O) was added, and then a temperature was decreased to −20° C. using saturated salt water and ice. After the temperature was checked, 8.6 mL of tert-butyl lithium (tert-BuLi, 14.66 mmol) was slowly dropped for about 30 minutes. At this time, the color was gradually changed to dark-brown, and when the dropping was completed, the mixed solution was stirred for 2 hours at the same temperature. After the mixed solution was stirred for 2 hours, 1.3 mL of DMF (16.62 mmol) was slowly dropped for about 5 minutes. When the injection was completed, the mixed solution was stirred for 1 hour at the same temperature, and at this time, the color was gradually changed to light-yellow. After being stirred for 1 hour, 10 mL of 4N HCl and 10 mL of primary distilled water were added and stirred for 10 minutes. After 10 minutes, an extraction process was performed using 300 mL of EtOAc, 100 mL of saturated salt water, and 200 mL of water. The organic layer (EtOAc) obtained through the extraction was concentrated by drying water existing in the organic layer with 15 g of anhydrous sodium sulfate and using an aspirator. A light-yellow solid compound obtained thus was separated (eluent: 20% EtOAc/Hexane) through a column chromatography method (6 cm of diameter, 15 cm of height) using a silica gel to obtain 1.27 g of a light-yellow solid compound 7 (50%). The product was analyzed by using a thin layer chromatography to have an elution value of R$_f$=0.25 (20% EtOAc/Hexane—eluting once). $^1$H NMR (CDCl$_3$, 300 MHz, 293K): δ 10.49(s, 1H), 8.25(s, 1H), 7.75-7.73(d, 1H), 7.29-7.24(d, 1H), 7.05-7.03 (dd, 1H), 6.77-6.76(d, 1H), 5.40(s, 2H), 3.59(s, 3H), 3.12(s, 6H). $^{13}$C NMR (CDCl$_3$, 75 MHz, 293K): δ 189.61, 155.99, 150.71, 139.74, 131.16, 130.89, 122.26, 121.29, 114.76, 107.66, 104.30, 94.75, 56.39, 40.32. HRMS: m/z calcd. for C$_{15}$H$_{17}$NO$_3$ 259.1208 found 259.1211.

(4) Synthesis of 6-(dimethylamino)-3-hydroxy-2-naphthaldehyde (compound of Chemical Formula 2)

The present inventors performed a synthesis of 6-(dimethylamino)-3-hydroxy-2-naphthaldehyde.

In detail, 195 mg of a compound 7 (0.75 mmol), 10 mL of isopropyl alcohol, and 5 mL of 5M HCl were added in a 25 mL round-bottom flask, and stirred at 60° C. for 3 hours. After 3 hours, the flask was cooled at room temperature, and then isopropyl alcohol was removed from the aspirator, and an extraction process was performed using 100 mL of ethyl acetate and 100 mL of water. The organic layer (EtOAc) obtained through the extraction was concentrated by drying water existing in the organic layer with 3 g of anhydrous sodium sulfate and using an aspirator. A yellow solid compound obtained thus was separated (eluent: 20% EtOAc/Hexane) through a column chromatography method (2 cm of diameter, 15 cm of height) using a silica gel to obtain 113 mg of a yellow compound of Chemical Formula 2 (70%). The product was analyzed by using a thin layer chromatography to have an elution value of R$_f$=0.35 (20% EtOAc/Hexane—eluting once). $^1$H NMR (CDCl$_3$, 300 MHz, 293K): δ 10.54(s, 1H), 9.89(s, 1H), 7.90(s, 1H), 7.70-7.67(d, 1H), 7.02-6.98(m, 2H), 6.66-6.65(d, 1H), 3.13(s, 6H). $^{13}$C NMR (CDCl$_3$, 75 MHz, 293K): δ 195.26, 156.83, 151.39, 140.62, 137.75, 130.87, 120.63, 119.03, 114.18, 108.73, 103.22, 40.26. HRMS: m/z calcd. for C$_{13}$H$_{13}$NO$_2$ 215.0946 found 259.0946.

(5) Synthesis of 8-(dimethylamino)-2-imino-2H-benzo[g]chromene-3-carbonitrile

The present inventors performed a synthesis of 8-(dimethylamino)-2-imino-2H-benzo[g]chromene-3-carbonitrile (compound of Chemical Formula 1).

In detail, 27 mg of a compound of Chemical Formula 2 (0.125 mmol), 66 mg of malononitrile (0.125 mmol), and 2 mL of ethanol (EtOH) were added in a 10 mL round-bottom flask. Thereafter, at room temperature, 124 μL of piperidine (1.25 mmol) was added and stirred for 1 hour. After 1 hour, ethanol was removed by using an aspirator. A red solid compound obtained thus was separated (eluent: 40% EtOAc/Hexane) through a column chromatography method (2 cm of diameter, 15 cm of height) using a silica gel to obtain 29.7 mg of a red solid compound of Chemical Formula 1 (90%). The product was analyzed by using a thin layer chromatography to have an elution value of R$_f$=0.35 (40% EtOAc—eluting once). $^1$H NMR (DMSO, 300 MHz, 293K): δ 8.75(s, 1H), 8.30(s, 1H), 7.90(s, 1H), 7.79-7.76(d, 1H), 7.24-7.15(m, 2H), 6.86(s, 1H), 3.08(s, 6H). $^{13}$C NMR (DMSO, 75 MHz, 293K): δ 152.11, 150.45, 150.21, 146.82, 137.81, 130.38, 130.20, 122.28, 115.91, 115.68, 113.37, 108.20, 103.83, 100.56. HRMS: m/z calcd. for $C_{13}H_{13}NO_2$ 263.1059 found 263.1058.

EXAMPLE 2

Confirmation of Fluorescence Characteristic of Compound 1 of Chemical Formula 1

Figure 1:
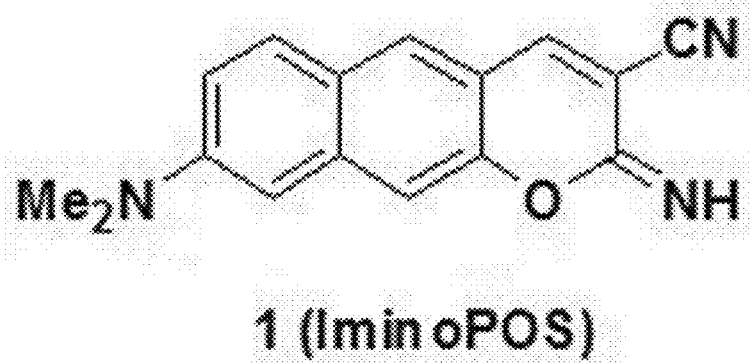
FIG. 1 illustrates a structure of a two-photon absorbing fluorescent substance (compound 1, IminoPOS) introduced in the present research.

The present inventors confirmed optical characteristics of the compound 1, which were illustrated in FIGS. 1, 2, and 3.

The present inventors used acedan and coumarin 153 as a comparative group when confirming the optical characteristics of the compound 1. The optical characteristics were measured at a concentration of 10 μM in an ethanol solvent. Quantum yield (ΦF) and two-photon absorption cross-section (GM) values were measured based on Rhodamine 6G (ΦF=0.6, GM=700). The compound 1 had an excitation wavelength of 446 nm and an emission wavelength of 585 nm. In addition, the compound 1 had high quantum yield of 0.67 and GM=126. On the contrary, acedan had the excitation wavelength of 365 nm and the emission wavelength of 501 nm, and coumarin 153 had the excitation wavelength of 425 nm and the emission wavelength of 548 nm. FIG. 2 arranges the respective optical characteristics, and FIG. 3 illustrates absorption and emission graphs.

The absorption and emission graphs were measured using an HP 8453 UV/Vis spectrophotometer and a Photon Technical International Fluorescence System, respectively, and a quartz cell of 1 cm was used. A self-made cavity-dumped Ti:sapphire oscillator pumped 5.0 W output frequency doubled Nd:YV04 laser (Verdi, Coherent) device was used in the measurement of the GM value. A reference excitation wavelength was 800 nm, an output pulse was 40 nJ, and a repetition rate was 380 kHz. A data processing method was a two-photon induced fluorescence (TPACS) method, and 1 GM was based on $10^{-50}$ $cm^4 s$ $photon^{-1} molecules^{-1}$.

EXAMPLE 3

Synthesis of Compounds of Chemical Formulas 3 and 4

A general synthesis path was illustrated in the following Scheme 2.

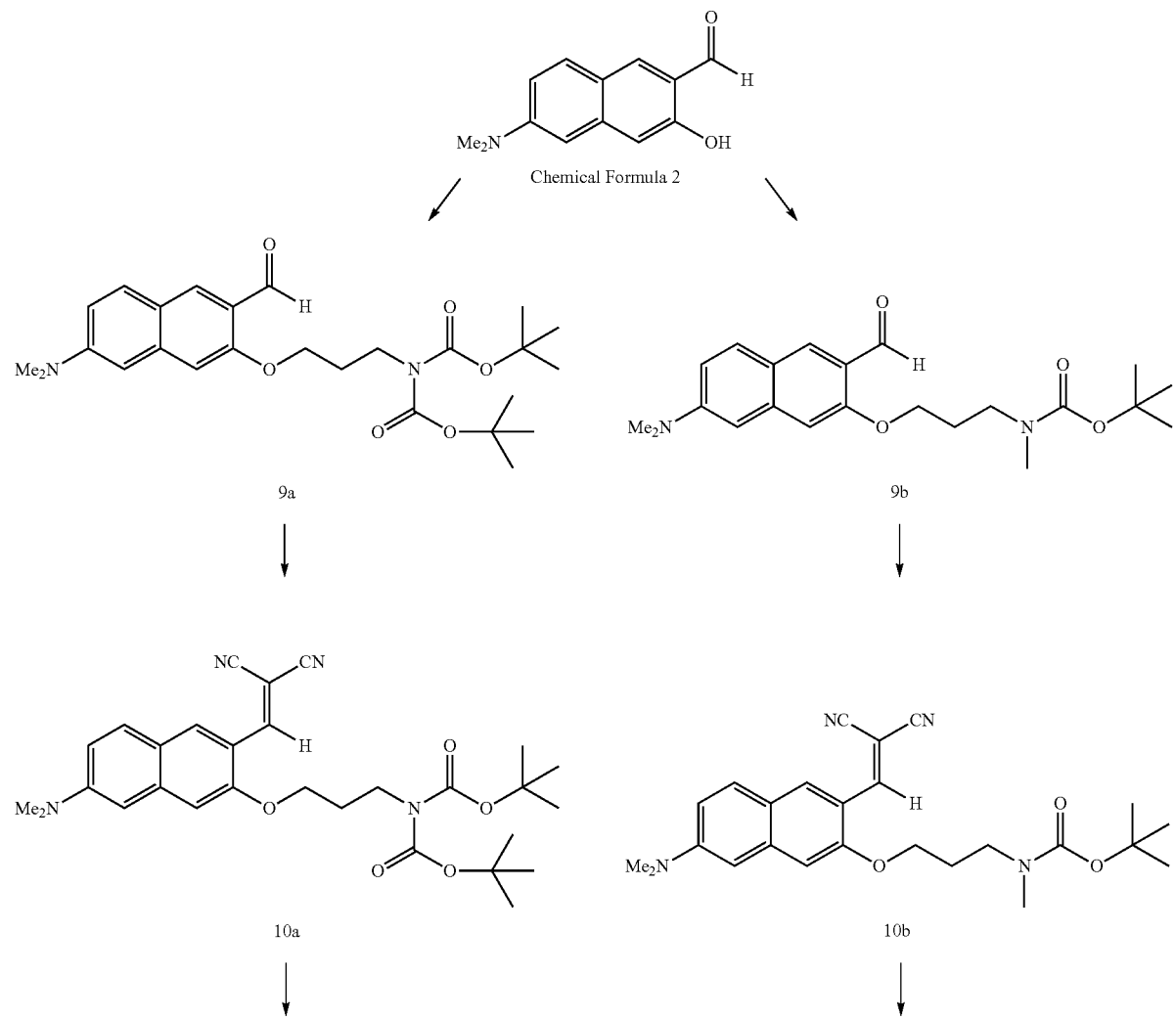

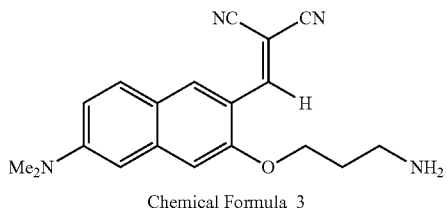

Chemical Formula 3

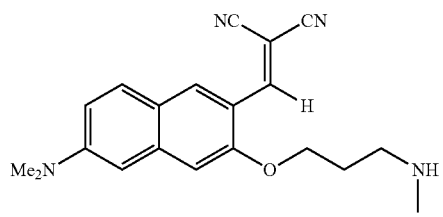

Chemical Formula 4

(1) Synthesis of 6-dimethylamino-3-{3-[N,N-bis(tert-butyloxycarbonyl)amino]propyloxy}naphthalene-2-carbaldehyde (compound 9a in Scheme 2)

The present inventors performed a synthesis of 6-dimethylamino-3-{3-[N,N-bis(tert-butyloxycarbonyl)amino]propyloxy}naphthalene-2-carbaldehyde.

In detail, 176.6 mg (0.82 mmol) of a compound of Chemical Formula 2, 242 mg (0.82 mmol) of N-tert-butyloxycarbonyl-3-(chloropropyl)carbamic acid tert-butyl ester, and 227 mg (1.64 mmol) of potassium carbonate were dissolved in 5 mL of DMF in a 25 mL round-bottom flask. The mixture was stirred at 50° C. for 27 hours. After 27 hours, the mixture was cooled at room temperature, and an extraction process was performed using 100 mL of EtOAc, 100 mL of water, and 100 mL of saturated salt water. The organic layer (EtOAc) obtained through the extraction was concentrated by drying water existing in the organic layer with 3 g of anhydrous sodium sulfate and using an aspirator. A yellow solid compound obtained thus was separated (eluent: 20% EtOAc/Hexane) through a column chromatography method (2 cm of diameter, 15 cm of height) using a silica gel to obtain 271 mg of a yellow solid compound of Chemical Formula 3 (71%). The product was analyzed by using a thin layer chromatography to have an elution value of $R_f$=0.35 (20% EtOAc—eluting once). $^1$H NMR (CDCl$_3$, 300 MHz, 293K): δ 10.51(s, 1H), 8.24(s, 1H), 7.73-7.71(d, 1H), 7.02-7.00(dd, 1H), 6.93 (s, 1H), 6.73-6.72(d, 1H), 4.22-4.19(t, 2H), 3.90-3.87(t, 2H), 3.12(s, 6H), 2.22-2.20(t, 2H), 1.51(s, 18H). $^{13}$C NMR (CDCl$_3$, 75 MHz, 293K): δ 189.70, 157.83, 152.63, 150.68, 139.88, 131.28, 130.38, 122.02, 120.66, 114.27, 104.47, 103.99, 82.47, 66.01, 43.94, 40.34, 28.84, 28.07. HRMS: m/z calcd. for $C_{26}H_{36}N_2O_6$ 472.2573 found 472.2571.

(2) Synthesis of 6-dimethylamino-3-{3-[N-methyl-N-(tert-butyloxycarbonyl)amino]propyloxy}naphthalene-2-carbaldehyde (compound 9b in Scheme 2)

The present inventors performed a synthesis of 6-dimethylamino-3-{3-[N-methyl-N-(tert-butyloxycarbonyl)amino]propyloxy}naphthalene-2-carbaldehyde.

The present synthesis method is the same as (1) of Example 3, and 3-chloropropyl-N-(methyl)carbamic acid tert-butyl ester instead of N-tert-butyloxycarbonyl-3-(chloropropyl)carbamic acid tert-butyl ester was used. A purification method was the same as (1) of Example 3, and a compound 9b was obtained with 70% yield. $^1$H NMR (CDCl$_3$, 300 MHz, 293K): δ 10.48(s, 1H), 8.21(s, 1H), 7.71-7.69(d, 1H), 7.00-6.98(dd, 1H), 6.92(s, 1H), 6.71-6.70(d, 1H), 4.17-4.15(t, 2H), 3.49-3.46(t, 2H), 3.10(s, 6H), 2.90(s, 3H), 2.12(s, 2H), 1.43(s, 9H). $^{13}$C NMR (CDCl$_3$, 75 MHz, 293K): δ 189.53, 157.73, 155.86, 150.75, 139.90, 131.28, 130.79, 121.99, 120.68, 114.31, 104.54, 103.98, 46.03, 40.33, 29.71, 29.26, 28.44, 14.13. HRMS: m/z calcd. for $C_{22}H_{30}N_2O_4$ 386.2206 found 386.2208.

(3) Synthesis of 2-{3-[N,N-bis(tert-butyloxycarbonyl)amino]propyloxy}-3-(2,2-dicyano)vinyl-7-(dimethylamino)naphthalene (compound 10a in Scheme 2)

The present inventors performed a synthesis of 2-{3-[N,N-bis(tert-butyloxycarbonyl)amino]propyloxy}-3-(2,2-dicyano)vinyl-7-(dimethylamino)naphthalene.

In detail, 152 mg (0.32 mmol) of the compound 9a and 43 mg (0.64 mmol) of malononitrile were dissolved in 3 mL of ethanol (EtOH) in a 10 mL round-bottom flask. An argon balloon was put, and 316 μL (3.2 mmol) of piperidine was slowly added at room temperature. The mixture was stirred at room temperature for 3 hours and then the solvent was removed using an aspirator. A dark-red solid compound obtained thus was separated (eluent: 30% EtOAc/Hexane) through a column chromatography method (2 cm of diameter, 15 cm of height) using a silica gel to obtain 151 mg of a dark-red solid compound 10a (90%). The product was analyzed by using a thin layer chromatography to have an elution value of $R_f$=0.30 (30% EtOAc—eluting once). $^1$H NMR (CDCl$_3$, 300 MHz, 293K): δ 8.71(s, 1H), 8.37(s, 1H), 7.72-7.70(d, 1H), 7.01-7.00(d, 1H), 6.87(s, 1H), 6.68-6.67(s, 1H), 4.16-4.14(t, 2H), 3.87-3.84(t, 2H), 3.16(s, 6H), 2.20(t, 2H), 1.52(s, 18H). $^{13}$C NMR (CDCl$_3$, 75 MHz, 293K): δ 155.00, 153.69, 152.62, 151.40, 140.12, 131.43, 131.15, 120.74, 117.18, 115.44, 114.47, 104.27, 103.76, 82.58, 66.23, 43.52, 40.28, 28.79, 28.79, 28.09. HRMS: m/z calcd. for $C_{29}H_{36}N_4O_5$ 520.2686 found 520.2689.

(4) Synthesis of 2-{3-[N-methyl-N-(tert-butyloxycarbonyl)amino]propyloxy}-3-(2,2-dicyano)vinyl-7-(dimethylamino)naphthalene (compound 10b in Scheme 2)

The present inventors performed a synthesis of 2-{3-[N-methyl-N-(tert-butyloxycarbonyl)amino]propyloxy}-3-(2,2-dicyano)vinyl-7-(dimethylamino)naphthalene.

The present synthesis method was the same as (3) of Example 3, and a compound 10b was obtained with 90% yield. $^1$H NMR (CDCl$_3$, 300 MHz, 293K): δ 8.36(s, 1H), 7.98(s, 1H), 7.45-7.42(d, 1H), 6.83-6.79(dd, 1H), 6.67(s, 1H), 6.51(s, 1H), 3.99-3.95(t, 2H), 3.36-3.32(t, 2H), 3.01(s, 6H), 2.81(s, 3H), 2.01-1.97(t, 2H), 1.33(s, 9H). $^{13}$C NMR (CDCl$_3$, 75 MHz, 293K): δ 155.74, 154.76, 152.94, 151.37, 140.15, 131.27, 130.83, 120.53, 116.77, 115.61, 114.51, 114.37, 104.11, 103.73, 79.47, 75.67, 66.00, 46.04, 40.17, 34.44, 28.40, 27.51. HRMS: m/z calcd. for $C_{25}H_{30}N_4O_3$ 434.2318 found 434.2319.

(5) Synthesis of 2-{[3-(3-aminopropoxy)-6-(dimethylamino)naphthalene-2-yl]methylene}malononitrile (compound of Chemical Formula 3)

The present inventors performed a synthesis of 2-{[3-(3-aminopropoxy)-6-(dimethylamino)naphthalene-2-yl]methylene}malononitrile.

In detail, 51.1 mg (0.1 mmol) of the compound 10a and 3 μL of triisopropylsilane were dissolved in 3 mL of dichloromethane and 3 mL of trifluoroacetic acid in a 25 mL round-bottom flask. An argon balloon was put, and the mixture was stirred at 0° C. for 1 hour and then concentrated using an aspirator. A dark-red solid compound (compound of Chemical Formula 3) obtained thus was utilized without an additional purification process. $^1$H NMR (CDCl$_3$, 300 MHz, 293K): δ 8.50(s, 1H), 8.43(s, 1H), 7.94(bs, 2H), 7.74-7.71(d, 1H), 7.14-7.10(m, 2H), 6.84-6.83(d, 1H), 4.24-4.22(t, 2H), 3.11(s, 6H), 3.10(m, 2H), 2.15-2.09(t, 2H). $^{13}$C NMR (CDCl$_3$, 75 MHz, 293K): δ 158.33, 157.96, 151.19, 139.74, 130.86, 130.53, 119.95, 116.52, 115.37, 114.81, 114.44, 104.64, 103.54, 76.16, 65.34, 36.43, 26.52.

(6) Synthesis of 2-({6-dimethylamino-3-[(3-methylamino)propoxy]-naphthalene-2-yl}methylene)malononitrile (compound of Chemical Formula 4)

The present inventors performed a synthesis of 2-({6-dimethylamino-3-[(3-methylamino)propoxy]-naphthalene-2-yl}methylene)malononitrile.

The present synthesis method was the same as (5) of Example 3. $^1$H NMR (CDCl$_3$, 300 MHz, 293K): δ 8.54(bs, 1H), 8.45(s, 1H), 8.42(s, 1H), 7.74-7.71(d, 1H), 7.14(s, 1H), 6.84-6.837.11-7.10(d, 1H), 6.83(d, 1H), 4.23-4.19(t, 2H), 3.20(m, 2H), 3.11(s, 6H), 2.64-2.63(t, 3H), 2.18-2.13(m, 2H). $^{13}$C NMR (CDCl$_3$, 75 MHz, 293K): δ 154.55, 154.25, 151.23, 139.75, 130.90, 130.61, 119.99, 116.51, 115.41, 114.87, 114.47, 104.68, 103.57, 76.27, 65.39, 45.84, 32.63, 25.18.

EXAMPLE 4

Confirmation of Fluorescence Characteristics of Compounds of Chemical Formulas 1, 3, and 4

The present inventors confirmed optical characteristics of the compounds 1, 3, and 4, and the optical characteristics were illustrated in FIG. 3.

The present inventors performed absorption and fluorescence emission experiments of the compounds 1, 3, and 4 in a buffer solution (100 mM HEPES, pH 7.4 with 5% glycerol and 1% DMSO) at a concentration of 10 μM, respectively. As absorbance spectra, an HP 8453 UV/Vis spectrophotometer and a Photon Technical International Fluorescence System were used. As a cell for fluorescence measurement, a quartz cell of 1 cm was used. The fluorescence graph was measured with an excitation wavelength of 448 nm. The top of FIG. 3 is the absorbance spectra, and the bottom is the emission graph.

EXAMPLE 5

Analysis of MAO Enzyme Activity Using Compounds of Chemical Formulas 3 and 4

Figure 8:
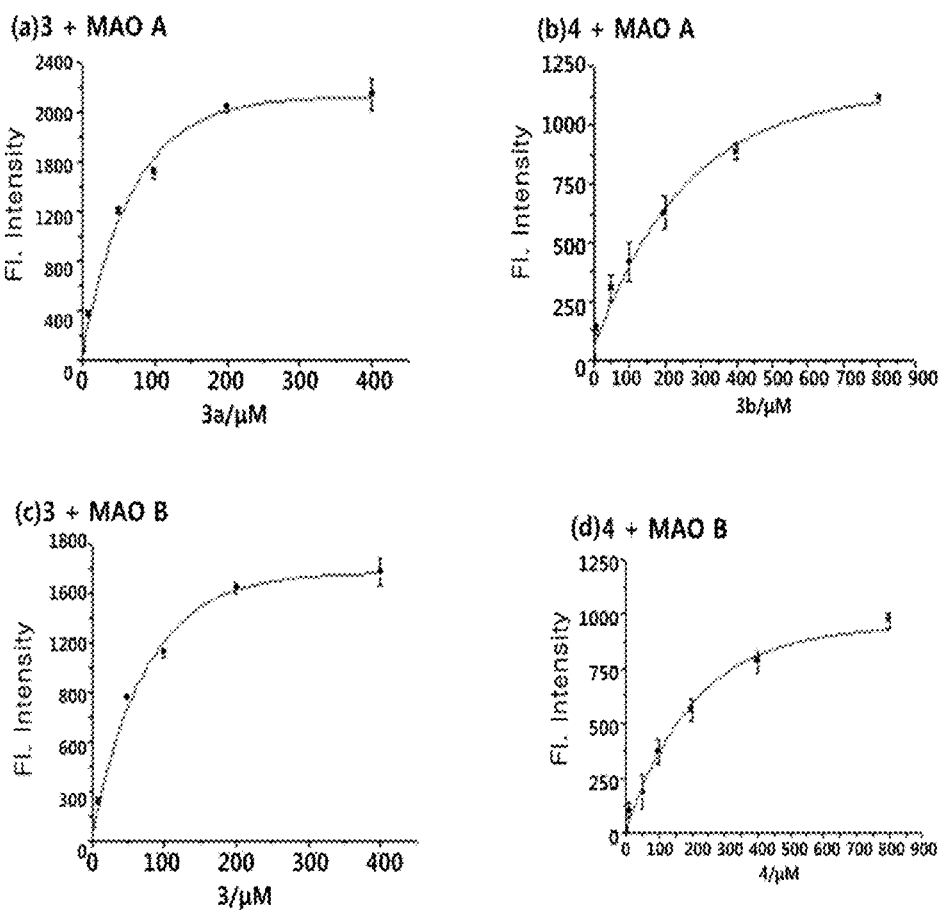
FIG. 8(a) is a result obtained by measuring enzyme activity with fluorescence intensity by adding MAO A enzyme and the compound of Chemical Formula 3 in the buffer solution.
FIG. 8(b) is a result obtained by measuring enzyme activity with fluorescence intensity by adding MAO A enzyme and the compound of Chemical Formula 4 in the buffer solution.
FIG. 8(c) is a result obtained by measuring enzyme activity with fluorescence intensity by adding MAO B enzyme and the compound of Chemical Formula 3 in the buffer solution.
FIG. 8(d) is a result obtained by measuring enzyme activity with fluorescence intensity by adding MAO B enzyme and a compound of Chemical Formula 4 in the buffer solution. Table illustrates values obtained by calculating a Michaelis-Menten constant from an enzyme activity graph.

The present inventors analyzed the MAO enzyme activity using the compounds of Chemical Formulas 3 and 4, and the MAO enzyme activity was illustrated in FIG. 8.

The present inventors performed enzyme kinetic assays using a 96-well fluorescence assay plate. The concentration of the compound of Chemical Formula 3 was used from 0 μM to 800 μM, MAO A and B enzymes were used with 10 μg/mL. The buffer solution was the same as Example 4, and the 96-well fluorescence assay plate was kept for 3 hours at 37° C. After 3 hours, the fluorescence intensity was measured by a microplate spectrofluorometer (VICTOR 3 VTM multilabel counter, Perkin Elmer-Wellesley, Mass., USA). The excitation wavelength was 465 nm, and the emission wavelength was recorded in 600 nm. Michaelis-Menten constants were calculated from an enzyme activity graph using an Origin program.

EXAMPLE 6

Figure 9:
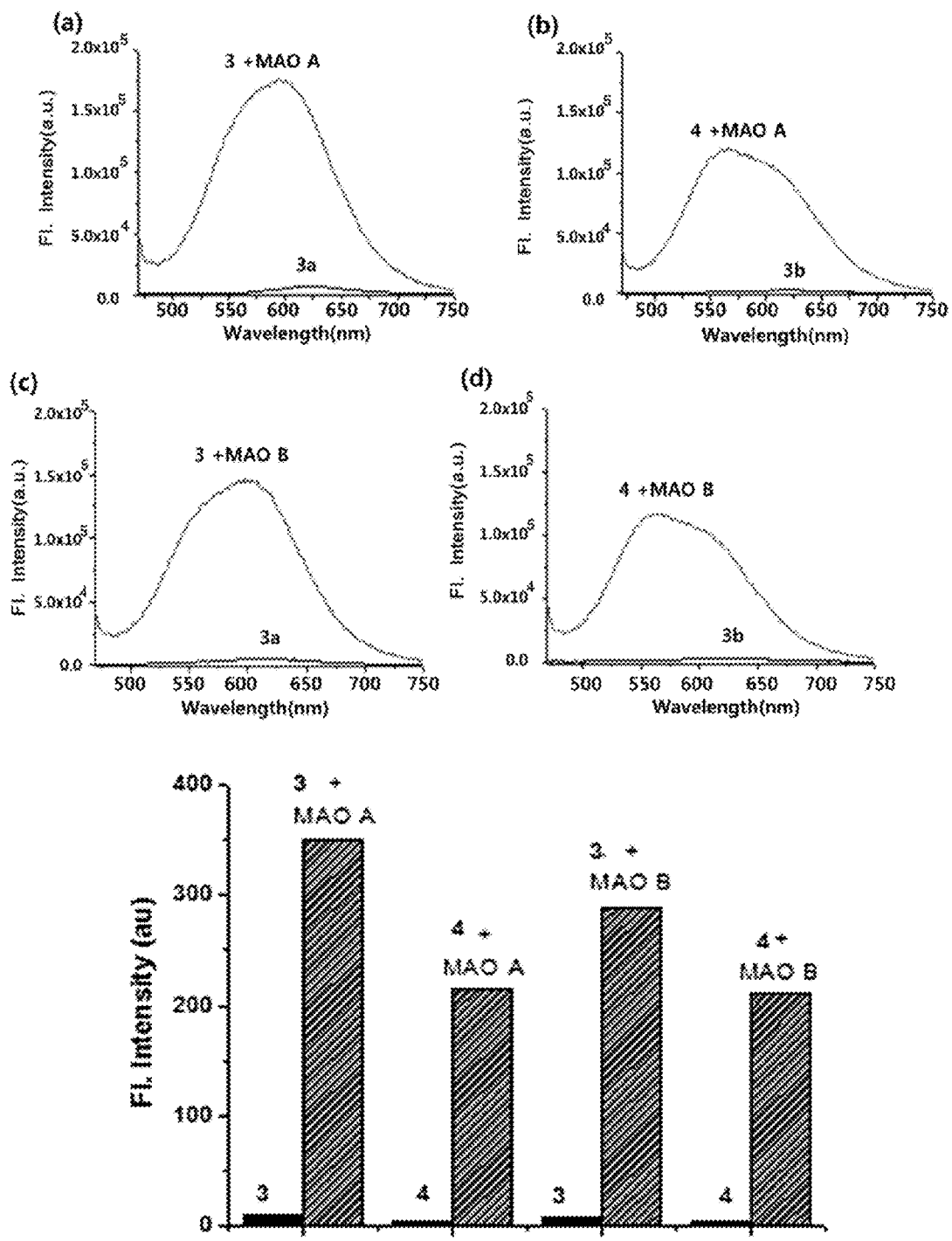
FIG. 9(a) is a graph illustrating intensities of fluorescence signals generated by reacting the compound of Chemical Formula 3 with MAO A.
FIG. 9(b) is a graph illustrating intensities of fluorescence signals generated by reacting the compound of Chemical Formula 4 with MAO A.
FIG. 9(c) is a graph illustrating intensities of fluorescence signals generated by reacting the compound of Chemical Formula 3 with MAO B.
FIG. 9(d) is a graph illustrating intensities of fluorescence signals generated by reacting the compound of Chemical Formula 4 with MAO B.

Fluorescence Observation of Reaction of Compounds of Chemical Formulas 3 and 4 and MAO Enzyme The present inventors observed a reaction with the MAO enzyme using the compounds of Chemical Formulas 3 and 4, and the observed reaction was illustrated in FIG. 9.

The present inventors used the compounds at the concentration corresponding to the Michaelis-Menten constants (Chemical Formula 3/MAO A; 70 μM, Chemical Formula 4/MAO B; 252 μM, Chemical Formula 3/MAO B; 75 μM, Chemical Formula 4/MAO B; 210 μM), and performed a fluorescence emission experiment of 50 μg/mL of the MAO enzyme in a buffer solution (100 mM HEPES, pH 7.4 with 5% glycerol and 1% DMSO). In the fluorescence graph measurement, the Photon Technical International Fluorescence system was used. As a cell for fluorescence measurement, a standard quartz cell having a width of 1 cm was used. The fluorescence graph was measured by the excitation wavelength of 448 nm after keeping the cell at 37° C. for 3 hours.

EXAMPLE 7

Figure 10:
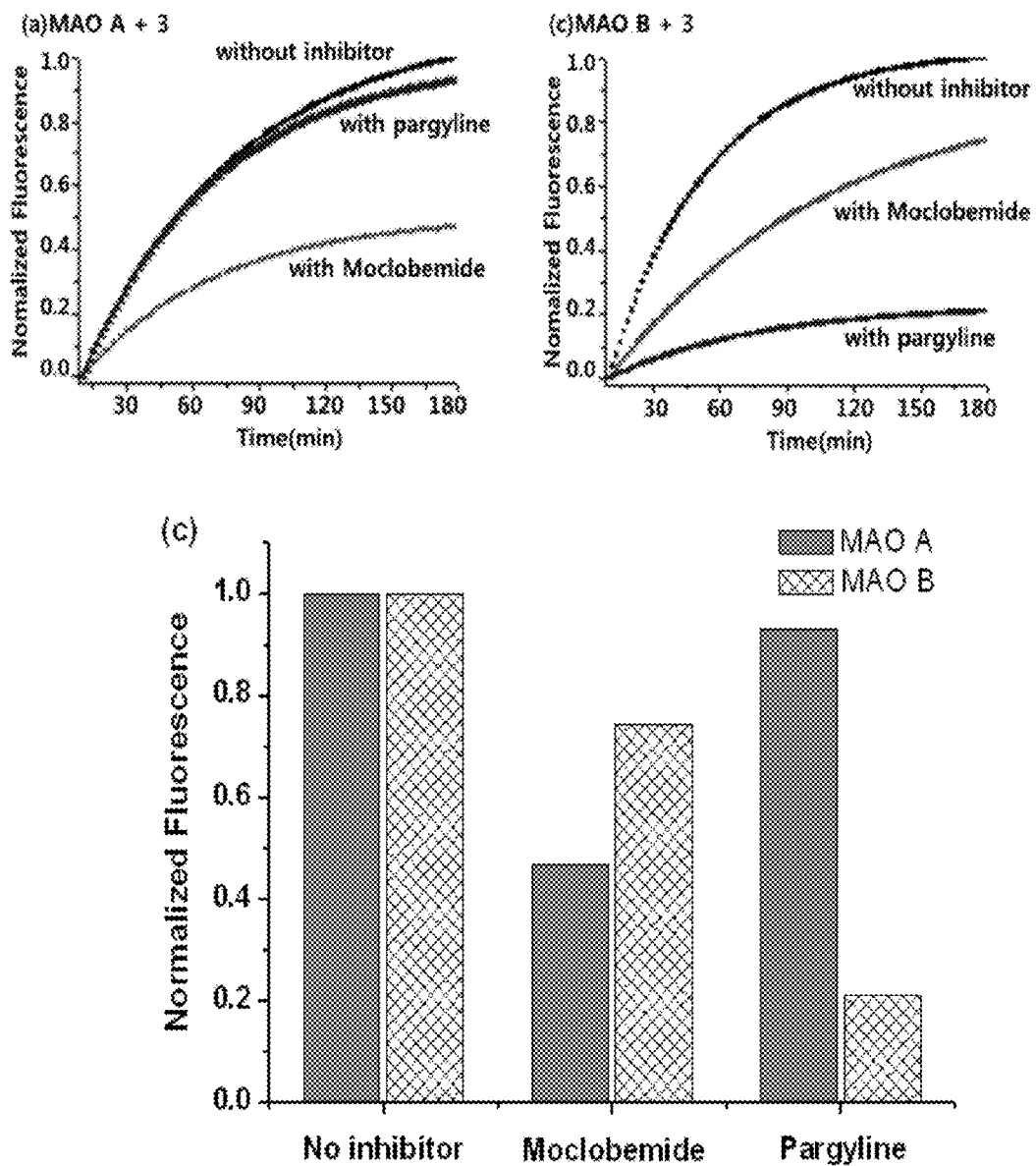
FIG. 10(a) is a graph illustrating intensities of fluorescence signals when adding mocolobemide and pargyline which are MAO enzyme inhibitors to a reaction between the compound of Chemical Formula 3 and MAO A.
FIG. 10(b) is a graph illustrating intensities of fluorescence signals when adding mocolobemide and pargyline which are MAO enzyme inhibitors to a reaction between the compound of Chemical Formula 3 and MAO B.
FIG. 10(c) is a bar graph displaying the normalized fluorescence at 180 min.

Confirmation for Effects of Compound of Chemical Formula 3 and MAO Enzyme Inhibitor The present inventors observed the enzyme activity of the MAO enzyme using the compound of Chemical Formula 3, and confirmed an effect of the MAO enzyme inhibitor at the same time, which were illustrated in FIG. 10.

The present inventors performed enzyme activity measurement and an enzyme inhibitor experiment using a 96-well fluorescence assay plate. Enzymes of 10 μg/mL of MAO A and 10 μg/mL of MAO B were kept for 2 hours at 37° C. with 70 μM of Moclobemide and 70 μM of Pargyline as inhibitors, respectively. Thereafter, 70 μM of the compound of Chemical Formula 3 was treated, and fluorescence was observed by a unit of 10 minutes for 3 hours. The buffer solution and the fluorescence observation method were the same as Example 4.

Moclobemide was known as an inhibitor of the MAO A enzyme, and Pargyline was known as an inhibitor of the MAO B enzyme. When the MAO A was treated with Moclobemide, an increase of fluorescence signals was small as compared with treatment with pargyline, and as a result, it was confirmed that activity of the MAO A was effectively inhibited by Moclobemide. Further, when the MAO B was treated with Pargyline, an increase of fluorescence signals was small as compared with treatment with Moclobemide, and as a result, it was confirmed that activity of the MAO B was inhibited by Pargyline.

EXAMPLE 8

One-photon Electron Microscopic Measurement of C6 Glioma Cell and Chromaffin Cell Treated with Compound of Chemical Formula 3 and Inhibitor The present inventors observed a fluorescence change in the C6 glioma cell and the Chromaffin cell treated with the compound 1 and the compound of Chemical Formula 3, respectively, and a fluorescence change treated with the MAO enzyme inhibitor through an one-photon electron microscope, and the fluorescence changes were illustrated in FIG. 11. The C6 glioma cell is a representative cell in which the MAO enzyme is not expressed (Aw, J. et al., Chem. Asian. J. 2010, 5, 1317.), and the Chromaffin cell is a cell known that the MAO B is overexpressed (Youdim, M. B. H. et al., Science 1984, 224, 619.).

The C6 glioma cell and the Chromaffin cell were prepared with the density of 2×10⁶ cells at a dish of 60 mm (Park, Y. et al., Endocrinology 2006, 147, 1349). Each cell was kept under a solvent condition of DMEM (Hyclone), 10% of fetal bovine serum (Hyclone), and 1% of antibiotics (WelGENE) and a condition of 5% $CO_2$-95% air at 37° C.

Cell fluorescence imaging was measured by using a fluorescence imaging microscope (Axiovert 200M, Carl Zeiss) after 100 μM of the compound 1 and the compound of Chemical Formula 3 were treated in respective cell dishes and kept for 1 hour under the same keeping condition. The compound which did not penetrate into the cell before the fluorescence measurement was removed through pipet suction, and a phosphate buffer saline (PBS) buffer solution was added, and then the fluorescence was observed. The excitation wavelength was 435 nm to 455 nm, and the emission wavelength was recorded in 555 to 575 nm.

In the case of the cell fluorescence imaging using the inhibitor, first, 100 μM of the inhibitor was treated in each cell dish, and the keeping process in the same condition as above was performed. Subsequently, 100 μM of the compound of Chemical Formula 3 was treated, and kept for 1 hour in the same condition, and then the fluorescence was measured.

In the case of the C6 glioma cell and the Chromaffin cell treated with the compound 1, bright one-photon cell images were provided (b and h of FIG. 11). In the case of the C6 glioma cell and the Chromaffin cell treated with the compound of Chemical Formula 3, in the C6 glioma cell in which the MAO was not expressed, IminoPOS was not generated, and thus the fluorescence was not shown (e of FIG. 11). However, in the case of the Chromaffin cell in which the MAO B was overexpressed, the IminoPOS was generated, and thus a bright cell image was provided (k of FIG. 11). In the case of the Chromaffin cell treated with Moclobemide as the MAO A inhibitor, the compound of Chemical Formula 3 normally generated the IminoPOS to provide the fluorescence (n of FIG. 11), while in the case of the Chromaffin cell treated with Pargyline as the MAO B inhibitor, the activity of the MAO B of the Chromaffin cell was inhibited and thus the IminoPOS was not generated, and as a result, the fluorescence was not observed (q of FIG. 11). Through the experiment, it was confirmed that the MAO B in the Chromaffin cell was overexpressed, and simultaneously, Pargyline was an effective MAO B enzyme activity inhibitor.

EXAMPLE 9

Two-photon Electron Microscopic Observation of C6 Glioma Cell and Chromaffin Cell Treated with Compound of Chemical Formula 3 and Inhibitor The present inventors observed fluorescence changes in the C6 glioma cell and the Chromaffin cell treated with the compound 1 and the compound of Chemical Formula 3, respectively, and a fluorescence change treated with the MAO enzyme inhibitor through a two-photon electron microscope, and the fluorescence changes were illustrated in FIG. 12. The preparing process of the cells and the fluorescence measuring method were the same as those in Example 8, and the two-photon electron microscope was used in the fluorescence observation.

The two-photon electron microscope was configured by an upright microscope (BX51, Olympus) and a 20-fold objective lens (XLUMPLFLN-W, NA 1.0 water immersion, Olympus), and a Ti:Sapphire laser (Chameleon Ultra, Coherent) was used. The fluorescence was observed at laser power of 10 mW, a two-photon excitation wavelength of 900 nm, an image photographing speed of 0.382 frame/sec.

Similarly to the result of the one-photon electron microscope, even in the result of the two-photon electron microscope, the compound 1 provided bright two-photon cell images (a and c of FIG. 12). Further, in the case of the C6 glioma cell treated with the compound of Chemical Formula 3, the fluorescence of the IminoPOS was not observed (b of FIG. 12), and in the Chromaffin cell, the generation of the IminoPOS was observed (d of FIG. 12). In the case of the cell treated with the inhibitor, the same result as the one-photon experiment was shown. In the case of the Chromaffin cell treated with Moclobemide, the generation of the IminoPOS was observed (e of FIG. 12), while in the case of the Chromaffin cell treated with Pargyline, the generation of the IminoPOS was not observed (f of FIG. 12).

EXAMPLE 10

Introduction of Vinyl Ether as an R group in Compound of Chemical Formula 5

(1) Synthesis Method

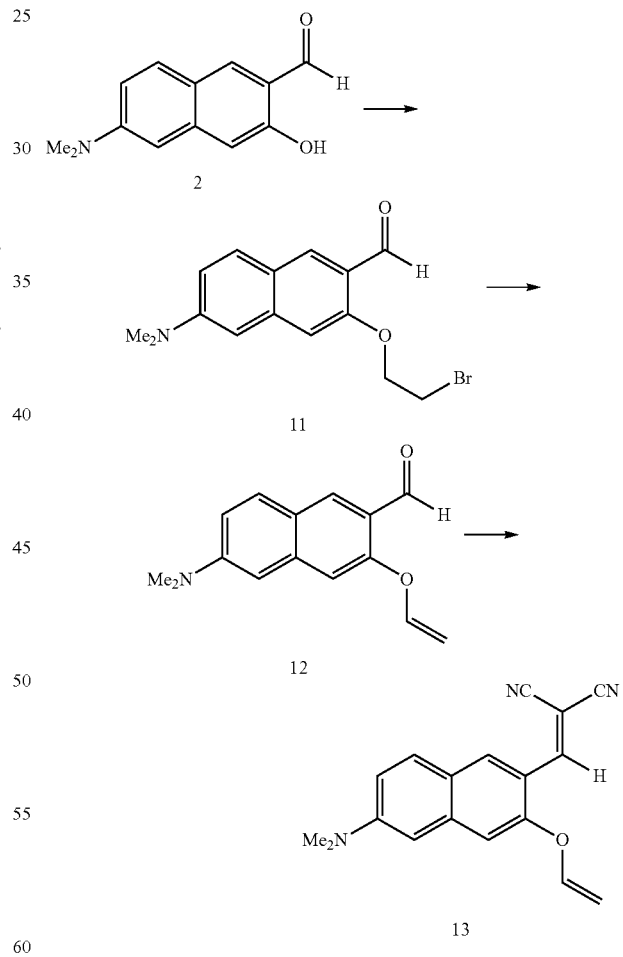

(Here, a Material 2 is the Chemical Formula 2)

(2) Detailed Contents of Experiment (a) Synthesis of 3-(2-bromoethoxy)-6-(dimethylamino)-2-naphthaldehyde (11)

150 mg (0.697 mmol) of the compound 2, 2.11 mL (24.69 mmol) of 1,2-dibromoethane, 0.3 mL (0.47 mmol) of Bu$_4$NOH, and 3.53 mL (25.63 mmol) of KOH were added, and stirred for 6 hours at 50° C. The mixture was separated and purified by a column chromatography (eluent: EtOAc/n-hexane(v/v)=1/9) without an additional extraction process to obtain 166 mg of a yellow solid compound 11 (74%). $^1$H NMR (CDCl$_3$, 300 MHz, 293K): δ 10.53(s, 1H), 8.26(s, 1H), 7.75-7.72(d, 1H), 7.05-6.94(m, 2H), 6.74-6.73(d, 1H), 4.51-4.47(t, 2H), 3.79-3.75(t, 2H), 3.13(s, 6H). $^{13}$C NMR (CDCl$_3$, 75 MHz, 293K); δ189.43, 156.96, 150.77, 139.67, 131.30, 130.84, 121.95, 120.93, 114.56, 104.99, 103.94, 67.94, 40.31, 28.82. HRMS: m/z calcd. for C$_{13}$H$_{13}$NO$_2$ 321.0364 found 321.0366.

(b) Synthesis of 6-(dimethylamino)-3-(vinyloxy)-2-naphthaldehyde) (12)

113 mg (0.35 mmol) of the compound 11 was dissolved in 5.6 mL of DMSO, and then 39 mg (0.347 mmol) of t-BuOK was added. The mixture was stirred for 3 hours at room temperature and then extracted by ethyl acetate and brine. The organic layer was dried with Na$_2$SO$_4$, and removed by vacuum-distillating the solvent. The mixture was separated and purified by a column chromatography (eluent: EtOAc/n-hexane(v/v)=1/9) to obtain 50 mg of a yellow solid compound 12 (59%). $^1$H NMR (CDCl$_3$, 300 MHz, 293K); δ 10.43(s, 1H), 8.28(s, 1H), 7.78-7.75(d, 1H), 7.10-7.05(m, 2H), 6.84-6.75(m, 2H), 4.94-4.88(d, 1H), 4.62-4.60(d, 1H), 3.13(s, 6H). $^{13}$C NMR (CDCl$_3$, 75 MHz, 293K); δ 189.02, 155.51, 150.75, 147.99, 139.45, 131.28, 130.96, 122.06, 121.98, 115.21, 109.94, 104.05, 96.63, 40.29. HRMS: m/z calcd. for C$_{15}$H$_{15}$NO$_2$ 241.1103 found 241.1105.

(c) Synthesis of 2-((6-(dimethylamino)-3-(vinyloxy)naphthalene-2-yl)methylene)malononitrile (13)

16 mg (0.066 mmol) of the compound 12 was dissolved in 1 mL of EtOH, and then added with 9 mg (0.14 mmol) of malononitrile and 0.06 mL (0.61 mmol) of piperidine, and stirred for 1 hour at room temperature. When the reaction was completed, EtOH was removed by vacuum-distillating, and then the mixture was separated and purified by a column chromatography (eluent: EtOAc/n-hexane(v/v)=1/3) without an additional extraction process to obtain 12 mg (63%) of an orange solid compound 13. $^1$H NMR (CDCl$_3$, 300 MHz, 293K); δ 8.75(s, 1H), 8.28(s, 1H), 7.77-7.73(d, 1H), 7.09-7.04(m, 2H), 6.74-6.67(m, 2H), 4.99-4.94(dd, 1H), 4.68-4.66 (dd, 1H), 3.17(s, 1H). $^{13}$C NMR (CDCl$_3$, 75 MHz, 293K); δ 153.40, 153.30, 151.70, 147.32, 139.88, 131.73, 131.45, 122.19, 117.18, 115.55, 115.46, 114.40, 109.34, 104.18, 98.19, 40.49. HRMS: m/z calcd. for C$_{18}$H$_{15}$N$_3$O 289.1215 found 289.1213.

(3) Experimental Result

The present inventors confirmed a fluorescence change characteristic for mercury ions (Hg ion) of the compound 13, and the fluorescence change characteristic was illustrated in FIG. 13.

The present inventors performed a fluorescence emission experiment of the compound 13 in a buffer solution (PBS, pH 7.4 with 5% DMSO) at a concentration of 3 μM. In the fluorescence measurement, the Photon Technical International Fluorescence System was used. As a cell for fluorescence measurement, a quartz cell of 1 cm was used. The fluorescence graph was measured with an excitation wavelength of 448 nm.

From the observed result, it was shown that as the concentration of the mercuric ions (HgCl$_2$) was increased, the fluorescence was increased (left graph). Further, from the result of observing the fluorescence change with time after adding 3 μM of the mercuric ions, it was observed that the fluorescence was increased as time passed (right graph).

EXAMPLE 11

Introduction of t-butyldimethylsilyl Ether as R Group in Compound of Chemical Formula 5

(1) Synthesis Method

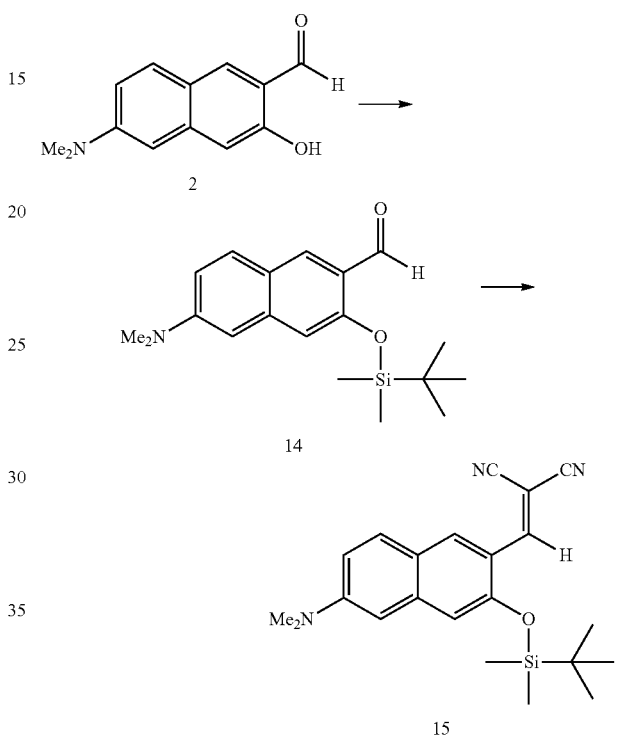

(Here, a material 2 is the Chemical Formula 2)

(2) Detailed Contents of Experiment (a) Synthesis of 3-(tert-butyldimethylsilyl)-6-(dimethylamino)-2-naphthaldehyde (14)

300 mg (1.394 mmol) of the compound 2 was dissolved in 10 mL of DCM and added with 5 mg (0.0187 mmol) of 4-dimethylaminopyridine (DMAP) and 0.2 ml (1.394 mmol) of Et$_3$N in sequence, and then a temperature was decreased to 0° C. using iced water. After the temperature was checked, 252.1 mg (1.6725 mmol) of t-butyldimethylsilyl chloride was slowly dissolved and added in 5 mL of DCM. The mixture was stirred for 12 hours while the temperature was changed to room temperature. After 12 hours, an extraction process was performed using 10 mL of a saturated NaHCO$_3$ aqueous solution and 60 mL of DCM. The DCM layer was separated and purified by a column chromatography (eluent: EtOAc/n-hexane(v/v)=1/4) after drying water using 5 g of MgSO$_4$ to obtain 415.7 mg (91%) of a yellow solid compound 14. $^1$H NMR (CDCl$_3$, 300 MHz, 293K): δ 10.45(s, 1H), 8.21(s, 1H), 7.72-7.69(d, 1H), 7.02-6.98(dd, 1H), 6.92(s, 1H), 6.66-6.65 (d, 1H), 3.10(s, 6H), 1.05(s, 9H), 0.32(s, 6H). $^{13}$C NMR (CDCl$_3$, 75 MHz, 293K): δ 190.07, 154.90, 150.57, 139.88, 131.25, 130.49, 124.02, 121.39, 111.72, 112.57, 103.61, 40.35, 25.80, 18.41, −4.25. HRMS: m/z calcd. for C$_{19}$H$_{27}$NO$_2$Si 329.1811 found 329.1808.

(b) Synthesis of 2-((6-(dimethylamino)-3-(tert-butyldimethylsilyl)naphthalene-2-yl)methylene)malononitrile (15)

415.7 mg (1.2616 mmol) of the compound 14 was dissolved in 9 mL of EtOH, and then added with 83.4 mg (1.2616 mmol) of malononitrile and 1 mL (12.616 mmol) of piperidine, and stirred for 3 hours at room temperature. When the reaction was completed, EtOH was removed by vacuum-distillating, and then the mixture was separated and purified by a column chromatography (eluent: EtOAc/n-hexane(v/v)=¼) without an additional extraction process to obtain 333.4 mg (70%) of an orange solid compound 15. $^1$H NMR (CDCl$_3$, 300 MHz, 293K): δ 8.70(s, 1H), 8.24(s, 1H), 7.70-7.67(d, 1H), 7.02-6.98(dd, 1H), 6.88(s, 1H), 6.60-6.59(d, 1H), 3.14 (s, 6H), 1.05(s, 9H), 0.31(s, 6H). $^{13}$C NMR(CDCl$_3$, 75 MHz, 293K): δ 154.13, 152.53, 151.30, 140.20, 131.43, 131.09, 121.46, 119.27, 115.40, 114.88, 114.30, 111.78, 103.41, 40.29, 25.79, 18.38, −4.23. HRMS: m/z calcd. for C$_{22}$H$_{27}$N$_3$OSi 377.1923 found 377.1923.

(3) Experimental Result

The present inventors confirmed a fluorescence change characteristic for fluoride ions (F ion) of the compound 15, and the fluorescence change characteristic was illustrated in FIG. 14.

The present inventors performed a fluorescence emission experiment of the compound 15 in 10 mM of a buffer solution (HEPES, pH 7.4 with 20% ACN) at a concentration of 20 μM. In the fluorescence measurement, the Photon Technical International Fluorescence System was used. As a cell for fluorescence measurement, a quartz cell of 1 cm was used. The fluorescence graph was measured with an excitation wavelength of 460 nm.

From the observed result, after adding 20 mM of the fluoride ions (NaF), it was observed that the fluorescence was increased with time (left graph). Further, from the result of confirming the fluorescence increase after adding various kinds of negative ions together with the compound 15 at the concentration of 20 μM, it was observed that only the fluoride ions were selectively reacted and thus the fluorescence increase was induced (right graph). The fluorescence intensity of the right graph was measured at 595 nm.

The two-photon absorbing fluorescent substance of the present invention can be used for an in-vivo imaging study because of absorption and emission in a longer wavelength than an existing fluorescent substance, and a precursor of the compound of Chemical Formula 1 can be used as a detection probe having high sensitivity and selectivity for each substrate due to high fluorescence sensitivity even in a one-photon microscope. Further, the compound of Chemical Formula 3 or Chemical Formula 4 of the present invention can be used in the study and treatment of diseases involved with the MAO enzyme.

Although a few embodiments of the present invention have been shown and described, it would be appreciated by those skilled in the art that changes may be made in these embodiments without departing from the principles and spirit of the invention, the scope of which is defined in the claims and their equivalents.

The invention claimed is:

1. A compound or a pharmaceutically acceptable salt thereof selected from the group consisting of:

[Chemical Formula 1]

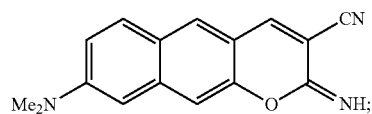

[Chemical Formula 2]

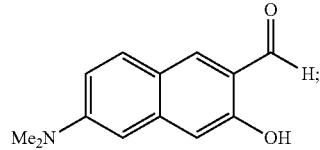

[Chemical Formula 3]

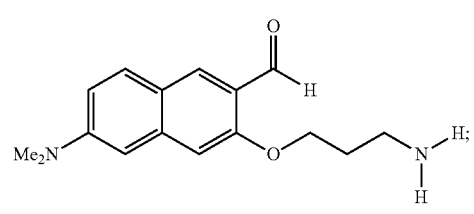

[Chemical Formula 4]

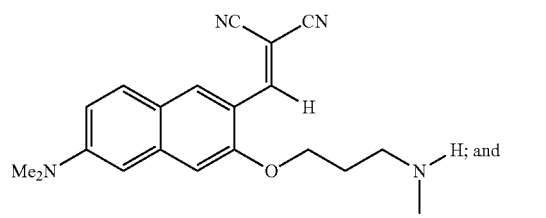

[Chemical Formula 5]

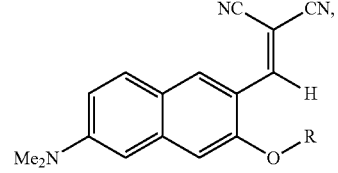

wherein, R is selected from the group consisting of vinyl, propargyl, 4-boronato-benzyl, t-butyldimethylsilyl, homoallyl and phosphate.

2. The compound of claim 1, comprising Chemical Formula 5 or a pharmaceutically acceptable salt thereof,

[Chemical Formula 5]

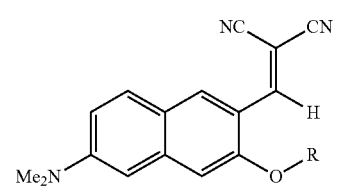

wherein, R is selected from the group consisting of vinyl, propargyl, 4-boronato-benzyl, t-butyldimethylsilyl, homoallyl, and phosphate.

3. The compound or the pharmaceutically acceptable salt thereof of claim 1, wherein the compound of Chemical Formula 1 is an one-photon or a two-photon absorbing fluorescent substance.

4. A method for preparing the compound of Chemical Formula 2 of claim 1, comprising:
 1) synthesizing 7-(dimethylamino)naphthalene-2-ol by adding sodium metabisuifite and an aqueous solution of dimethylamine to 2,7-dihydroxy naphthalene;
 2) synthesizing 7-(methoxymethoxy)-N,N-dimethylnaphthalene-2-amine by adding sodium hydride and chloromethyl methyl ether to the 7-(dimethylamino)naphthalene-2-ol obtained from step (1);

3) synthesizing 6-(dimethylamino)-3-(methoxymethoxy)-2-naphthaldehyde by adding ethyl ether, and tertiary butyllithium, and N,N-dimethylformamide to the 7-(methoxymethoxy)-N,N-dimethylnaphthalene-2-amine obtained from step (2); and
4) adding isopropyl alcohol and HCl to the 6-(dimethylamino)-3-(methoxymethoxy)-2-naphthaldehyde obtained from step (3) to obtain the compound of Chemical Formula 2.

5. A method for preparing the compound of Chemical Formula 1 of claim 1 comprising adding malononitrile and piperidine to the compound of Chemical Formula 2 of claim 1 to obtain the compound of Chemical Formula 1.

6. A method for preparing the compound of Chemical Formula 3 of claim 1, comprising:
   1) synthesizing 6-dimethylamino-3-{3-[N,N-bis(tert-butyloxycarbonyl)amino]propyloxy}naphthalene-2-carbaldehyde by adding N-ter-butyloxycarbonyl-3-(chloropropyi)carbamic acid tert-butyl ester and potassium carbonate to the compound of Chemical Formula 2 of claim 1;
   2) synthesizing 2-{3-[N,N-bis(tert-butyloxycarbonyl)amino]propyloxy }-3-(2,2,-dicyano)vinyl-7-(dimethylamino)naphthalene by adding malononitrile and piperidine to the 6-dimethylamino-3-{3-[N,N-bis(tert-butyloxycarbonyl)amino]propyloxy }naphthalene-2-carbaldehyde obtained from step (1); and
   3) adding triisopropylsilane to the 2-{3-[N,N-bis(tert-butyloxycarbonyl)amino]propyloxy }-3-(2,2,-dicyano)vinyl-7-(dimethylamino)naphthalene obtained from step (2) to obtain the compound of Chemical Formula 3.

7. A method for preparing the compound of Chemical Formula 4 of claim 1, comprising:
   1) synthesizing 6-dimethylamino-3-{3-[N-methly-N-(tert-butyloxycarbonyl)amino]propyloxy}naphthalene-2-carbaldehyde by adding [3-chloropropyl-N-(methyl) carbamic acid tert-butyl ester]and potassium carbonate to the compound of the Chemical Formula 2 of claim 1;
   2) synthesizing [2-{3-[N-methyl-N-(tert-butyloxycarbonyl)amino]propyloxy}-3-(2,2-dicyano)vinyl-7-(dimethylamino)naphthalene] by adding malononitrile and piperidine to the 6-dimethylamino-3-{3-[N-methly-N-(tert-butyloxycarbonyl)amino]propyloxy }naphthalene-2-carbaldehyde obtained from step (1); and
   3) adding triisopropylsilane to the [2-{3-N-methyl-N-(tert-butyloxycarbonyl)amino]propyloxy}-3-(2,2-dicyano) vinyl-7-(dimethylamino)naphthalene]
   obtained from step (2) to obtain the compound of Chemical Formula 4.

8. A method for preparing the compound of Chemical Formula 5 of claim 1, comprising:
   1) synthesizing 3-(2-bromoethoxy)-6-(dimethylamino)-2-naphthaldehyde by adding 1,2-dibromoethane, $Bu_4NOH$, and KOH to the compound of Chemical Formula 2;
   2) synthesizing 6-(dimethylamino)-3-(vinyloxy)-2-naphthaldehyde by adding t-BuOK to the 3-(2-bromoethoxy)-6-(dimethylamino)-2-naphthaldehyde obtained from step (1); and
   3) synthesizing 2-((6-dimethylamino)-3-(vinyloxy)naphthalen-2-yl)methylene)malononitrile by adding malononitrile and piperidine to the 6-(dimethylamino)-3-(vinyloxy)-2-naphthaldehyde obtained from step (2) to obtain the compound of Chemical formula 5, wherein R is vinyl.

9. A method for preparing the compound of Chemical Formula 5 of claim 1, wherein R is t-butyldimethylsilyl, comprising:
   1) synthesizing 3-(tert-butyldimethylsilyl)oxy)-6-(dimethylamino)-2-naphthaldehyde by adding 4-dimethylaminopyridine, $Et_3N$, and t-butyldimethylsilyl chloride to the compound of the Chemical Formula 2 of claim 1; and
   2) synthesizing 2-((3-((tert-butyldimethylsilyl)oxy)-6-(dimethylamino)naphthalen-2-yl)methylene)malononitrile by adding malononitrile and piperidine to the 3-(tert-butyldimethylsilyl)-6(dimethylamino)-2-naphthaldehyde obtained from step (1) to obtain the compound of Chemical Formula 5, wherein R is t-butyldimethylsilyl.

10. A method for screening a test compound for monoamine oxidase inhibitory activity, comprising the steps of:
   a) measuring the fluorescence of the compound of Chemical Formula 3 or Chemical Formula 4 of claim 1 in the absence of the test compound;
   b) contacting the test compound with monoamine oxidase in the presence of the compound of Chemical Formula 3 or Chemical Formula 4 of claim 1; and
   (c) detecting fluorescence generated from step (b) wherein decreased fluorescence associated with the contacting step compared to the measured fluorescence corresponding to Chemical Formula 3 or Chemical Formula 4 in step (a) indicates that the test compound is a monoamine oxidase inhibitor.

11. A method for measuring the enzyme activity of a monoamine oxidase in a solution comprising
   contacting the solution with the compound of Chemical Formula 3 or Chemical Formula 4 of claim 1;
   detecting a change in the fluorescence associated with the contacting step; and
   correlating the change in fluorescence with monoamine oxidase activity in the solution.

12. A method for imaging a cell comprising contacting a cell with the compound of Chemical Formula 1 of claim 1, allowing the cell to uptake the compound of Chemical Formula 1 and exposing the contacted cell to light at a frequency known to cause the compound of Chemical Formula 1 to fluoresce, thereby imaging the cell.

13. A probe for detection of a mercury on comprising the compound of Chemical Formula 5 of claim 1 in which R is vinyl.

14. A probe for detection of a palladium on comprising the compound of Chemical Formula 5 of claim 1 in which R is propargyl.

15. A probe for detection of hydrogen peroxide comprising the compound of Chemical Formula 5 of claim 1 in which R is 4-boranato-benzyl.

16. A probe for detection of a fluoride on comprising the compound of Chemical Formula 5 of claim 1 in which R is t-butyldimethylsilyi.

17. A probe for detection of ozone comprising the compound of Chemical Formula 5 of claim 1 in which R is bromoallyl.

18. A probe for detection of a phosphatase comprising the compound of Chemical Formula 5 of claim 1 in which R is phosphate.

19. A probe for the detection of monoamine oxidase (MAO) comprising the compound of Chemical Formula 3 or Chemical Formula 4 of claim 1.

20. A method for imaging a cell containing MAO comprising contacting a cell with the compound of Chemical formula 3 or Chemical Formula 4 of claim 1 and exposing the contacted cell to light at a wavelength between 350 nm and 550 nm where a contacted cell containing MAO fluoresces, thereby imaging the cell.

* * * * *